US008304381B2

(12) United States Patent
Chen

(10) Patent No.: US 8,304,381 B2
(45) Date of Patent: Nov. 6, 2012

(54) HUMAN PROLACTIN ANTAGONIST-ANGIOGENESIS INHIBITOR FUSION PROTEINS

(75) Inventor: Wen Y. Chen, Clemson, SC (US)

(73) Assignee: Oncolix, Inc., Houston, TX (US)

( * ) Notice: Subject to any disclaimer, the term of this patent is extended or adjusted under 35 U.S.C. 154(b) by 320 days.

(21) Appl. No.: 12/010,395

(22) Filed: Jan. 24, 2008

(65) Prior Publication Data
US 2009/0088375 A1 Apr. 2, 2009

Related U.S. Application Data

(62) Division of application No. 10/449,609, filed on Jun. 2, 2003, now Pat. No. 7,339,027.

(60) Provisional application No. 60/384,121, filed on May 31, 2002.

(51) Int. Cl.
*A01N 37/18* (2006.01)
(52) U.S. Cl. .......................................... 514/1.1; 514/19.3
(58) Field of Classification Search ........................ None
See application file for complete search history.

(56) References Cited

U.S. PATENT DOCUMENTS 6,342,221 B1 1/2002 Thorpe et al.
6,803,211 B2 * 10/2004 Tong et al. .................... 435/69.1

FOREIGN PATENT DOCUMENTS
WO    WO 01/70985    9/2001

OTHER PUBLICATIONS

Gura, Science, 1997, 278:1041-1042.*
Database DISSABS on STN, AN 2003:.7678, Beck et al., "Relationship of the prolactin antagonist, G129R, with Bcl-2 and its therapeutic effects as a fusion protein with endostatin for the treatment of breast cancer", Dissertation Abstracts International, 2002, vol. 63, No. 11B, p. 5056.
Malonne et al., "Mechanisms of Tumor Angiogenesis and Therapeutic Implications: Angiogenesis Inhibitors," vol. 17, No. 1, 1999, pp. 1-14.
Chen et al., "In vivo Studies of the Anti-Tumor Effects of a Human Prolactin Antagonist, HPRL-G129R," vol. 20, Apr. 2002, pp. 813-818.
Beck et al., "Prolactin Antagonist-Endostatin Fusion Protein as a Targeted Dual-Functional Therapeutic Agent for Breast Cancer," vol. 63, No. 13, Jul. 2003, pp. 3598-3604.
Llovera et al., "Human Prolactin (HPRL) Antagonists Inhibit HPRL-Activated Signaling Pathways Involved in Breast cancer Cell Proliferation," vol. 19, No. 41, Sep. 2000, pp. 4695-4705.
Clevenger et al., "Expression of Prolactin and Prolactin Receptor in Human Breast Carcinoma", American Journal of Pathology, vol. 146, No. 3, pp. 695-705, Mar. 1995.
Ginsburg et al., "Prolactin Synthesis and Secretion by Human Breast Cancer Cells", Cancer Research, vol. 55, No. 11, pp. 2591-2595, Jun. 1995.
Wennbo et al., "Transgenic Mice Overexpressing the Prolactin Gene Develop Dramatic Enlargement of the Prostate Gland", Endocrinology, vol. 138, No. 10, pp. 4410-4415, Apr. 1997.
Aragona et al., "Specific Prolactin Binding Sites in the Prostate and Testis of Rats", Endocrinology, vol. 97, No. 3, pp. 677-684, Jan. 1975.
Leake et al., "Characterization of the Prolactin Receptor in Human Prostate", Journal of Endocrinology, vol. 99, pp. 321-328, Apr. 1983.
Hammond et al., "Serum FSH, LH and Prolactin and Nomal Males and Patients with Prostatic Diseases", Clinical Endocrinology, vol. 7, No. 2, pp. 129-135, Aug. 1977.
"Influence of Age on Serum Prolactin Levels in Women and Men", British Medical Journal, vol. 4, No. 5999, pp. 738-739, Dec. 1975.
Zhang et al., "A Novel Design of Targeted Endocrine and Cytokine Therapy for Breast Cancer", Clinical Cancer Research, vol. 8, pp. 1196-1205, Apr. 2002.
Chen et al., "A Human Prolactin Antagonist, hPRL-G129R, Inhibits Breast Cancer Cell Proliferation through Induction of Apoptosis", Clinical Cancer Research, vol. 5, pp. 3583-3593, Nov. 1999.
Altschul et al., "Basic Local Alignment Search Tool", Journal of Molecular Biology, vol. 215, No. 3, pp. 403-410, Oct. 1990.
Gish et al., "Identification of Protein Coding Regions by Database Similarity Search", Nature Genetics, vol. 3, No. 3, pp. 266-272, Mar. 1993.
Madden et al., "Applications of Network Blast Server", Methods in Enzymology, vol. 266, pp. 131-141, 1996.
Altschul et al., "Gapped Blast and PSI-BLAST: A New Generation of Protein Database Search Progams", Nucleic Acids Research, vol. 25, No. 17, pp. 3389-3402, Sep. 1997.
Zhang et al., "PowerBLAST: A New Network Blast Application for Interactive or Automated Sequence Analysis and Annotation", Genome Research, vol. 7, pp. 649-656, 1997.
Osol, Arthur, Remington's 16th Edition, Pharmaceutical Sciences, 1980. (Table of Contents).

* cited by examiner

*Primary Examiner* — Misook Yu
*Assistant Examiner* — Mark Halvorson
(74) *Attorney, Agent, or Firm* — Morgan, Lewis & Bockius LLP

(57) ABSTRACT

A novel fusion protein, comprising a receptor-antagonizing domain and an angiogenesis inhibiting domain, characterized, for example, by its ability to block apoptosis and/or inhibit endocrine response, is useful in treating cancer. For example, a human prolactin antagonist-endostatin fusion protein combines apoptosis induction and angiogenesis inhibition to combat cancer.

3 Claims, 19 Drawing Sheets

FIG. 1A
hPRL-G129R (603bp)

ATGttgccca tctgtcccgg cggggctgcc cgatgccagg tgacccttcg agacctgttt
gaccgcgccg tcgtcctgtc ccactacatc cataacctct cctcagaaat gttcagcgaa
ttcgataaac ggtataccca tggccggggg ttcattacca aggccatcaa cagctgccac
acttcttccc ttgccacccc cgaagacaag gagcaagccc aacagatgaa tcaaaaagac
tttctgagcc tgatagtcag catattgcga tcctggaatg agcctctgta tcatctggtc
acggaagtac gtggtatgca agaagcccg gaggctatcc tatccaaagc tgtagagatt
gaggagcaaa ccaaacggct tctagagCGC atggagctga tagtcagcca ggttcatcct
gaaaccaaag aaaatgagat ctaccctgtc tggtcgggac ttccatccct gcagatggct
gatgaagagt ctcgcctttc tgcttattat aacctgctcc actgcctacg cagggattca
cataaaatcg acaattatct caagctcctg aagtgccgaa tcatccacaa caacaactgc
TAG

FIG. 1B
Amino Acid Sequence (200)

MLPICPGGAARCQVTLRDLFDRAVVLSHYIHNLSSEMFSEFDKRYTHGRGFITKA
INSCHTSSLATPEDKEQAQQMNQKDFLSLIVSILRSWNEPLYHLVTEVRGMQEAP
EAILSKAVEIEEQTKRLLERMELIVSQVHPETKENEIYPVWSGLPSLQMADEESRL
SAYYNLLHCLRRDSHKIDNYLKLLKCRIIHNNNC*stop*

FIG. 1C
Endostatin (555bp)

ATGcacagcc accgcgactt ccagccggtg ctccacctgg ttgcgctcaa cagcccctg
tcaggcggca tgcggggcat ccgcggggcc gacttccagt gcttccagca ggcgcgggcc
gtggggctgg cgggcacctt ccgcgccttc ctgtcctcgc gcctgcagga cctgtacagc
atcgtgcgcc gtgccgaccg cgcagccgtg cccatcgtca acctcaagga cgagctgctg
tttcccagct gggaggctct gttctcaggc tctgagggtc cgctgaagcc cggggcacgc
atcttctcct ttgacggcaa ggacgtcctg aggcacccca cctggcccca aagagcgtg
tggcatggct cggaccccaa cgggcgcagg ctgaccgaga gctactgtga gacgtggcgg
acggaggctc cctcggccac gggccaggcc tcctcgctgc tgggggcag gctcctgggg
cagagtgccg cgagctgcca tcacgcctac atcgtgctct gcattgagaa cagcttcatg
actgcctcca agTAG

FIG. 1D
Amino Acid Sequence (184)

MHSHRDFQPVLHLVALNSPLSGGMRGIRGADFQCFQQARAVGLAGTFRAFLSSR
LQDLYSIVRRADRAAVPIVNLKDELLFPSWEALFSGSEGPLKPGARIFSFDGKDVL
RHPTWPQKSVWHGSDPNGRRLTESYCETWRTEAPSATGQASSLLGGRLLGQSA
ASCHHAYIVLCIENSFMTASK*stop*

FIG. 1E hPRL-G129R-Endostatin Fusion Protein (GEFP) (1,155bp)

```
ATGttgccca tctgtcccgg cggggctgcc cgatgccagg tgacccttcg agacctgttt
gaccgcgccg tcgtcctgtc ccactacatc cataacctct cctcagaaat gttcagcgaa
ttcgataaac ggtataccca tggccggggg ttcattacca aggccatcaa cagctgccac
acttcttccc ttgccacccc cgaagacaag gagcaagccc aacagatgaa tcaaaaagac
tttctgagcc tgatagtcag catattgcga tcctggaatg agcctctgta tcatctggtc
acggaagtac gtggtatgca agaagccccg gaggctatcc tatccaaagc tgtagagatt
gaggagcaaa ccaaacggct tctagagCGC atggagctga tagtcagcca ggttcatcct
gaaaccaaag aaaatgagat ctaccctgtc tggtcgggac ttccatccct gcagatggct
gatgaagagt ctcgcctttc tgcttattat aacctgctcc actgcctacg cagggattca
cataaaatcg acaattatct caagctcctg aagtgccgaa tcatccacaa caacaactgc
GGATCCcaca gccaccgcga cttccagccg gtgctccacc tggttgcgct caacagcccc
ctgtcaggcg gcatgcgggg catccgcggg gccgacttcc agtgcttcca gcaggcgcgg
gccgtggggc tggcgggcac cttccgcgcc ttcctgtcct cgcgcctgca ggacctgtac
agcatcgtgc gccgtgccga ccgcgcagcc gtgcccatcg tcaacctcaa ggacgagctg
ctgtttccca gctgggaggc tctgttctca ggctctgagg gtccgctgaa gcccggggca
cgcatcttct cctttgacgg caaggacgtc ctgaggcacc ccacctggcc ccagaagagc
gtgtggcatg gctcggaccc caacgggcgc aggctgaccg agagctactg tgagacgtgg
cggacggagg ctccctcggc cacgggccag gcctcctcgc tgctgggggg caggctcctg
ggcagagtg ccgcgagctg ccatcacgcc tacatcgtgc tctgcattga aacagcttc
atgactgcct ccaagTAG
```

FIG. 1F

Amino Acid Sequence (385)

MLPICPGGAARCQVTLRDLFDRAVVLSHYIHNLSSEMFSEFDKRYTHGRGFITKA
INSCHTSSLATPEDKEQAQQMNQKDFLSLIVSILRSWNEPLYHLVTEVRGMQEAP
EAILSKAVEIEEQTKRLLERMELIVSQVHPETKENEIYPVWSGLPSLQMADEESRL
SAYYNLLHCLRRDSHKIDNYLKLLKCRIIHNNNCGSHSHRDFQPVLHLVALNSPL
SGGMRGIRGADFQCFQQARAVGLAGTFRAFLSSRLQDLYSIVRRADRAAVPIVN
LKDELLFPSWEALFSGSEGPLKPGARIFSFDGKDVLRHPTWPQKSVWHGSDPNG
RRLTESYCETWRTEAPSATGQASSLLGGRLLGQSAASCHHAYIVLCIENSFMTAS
K*stop*

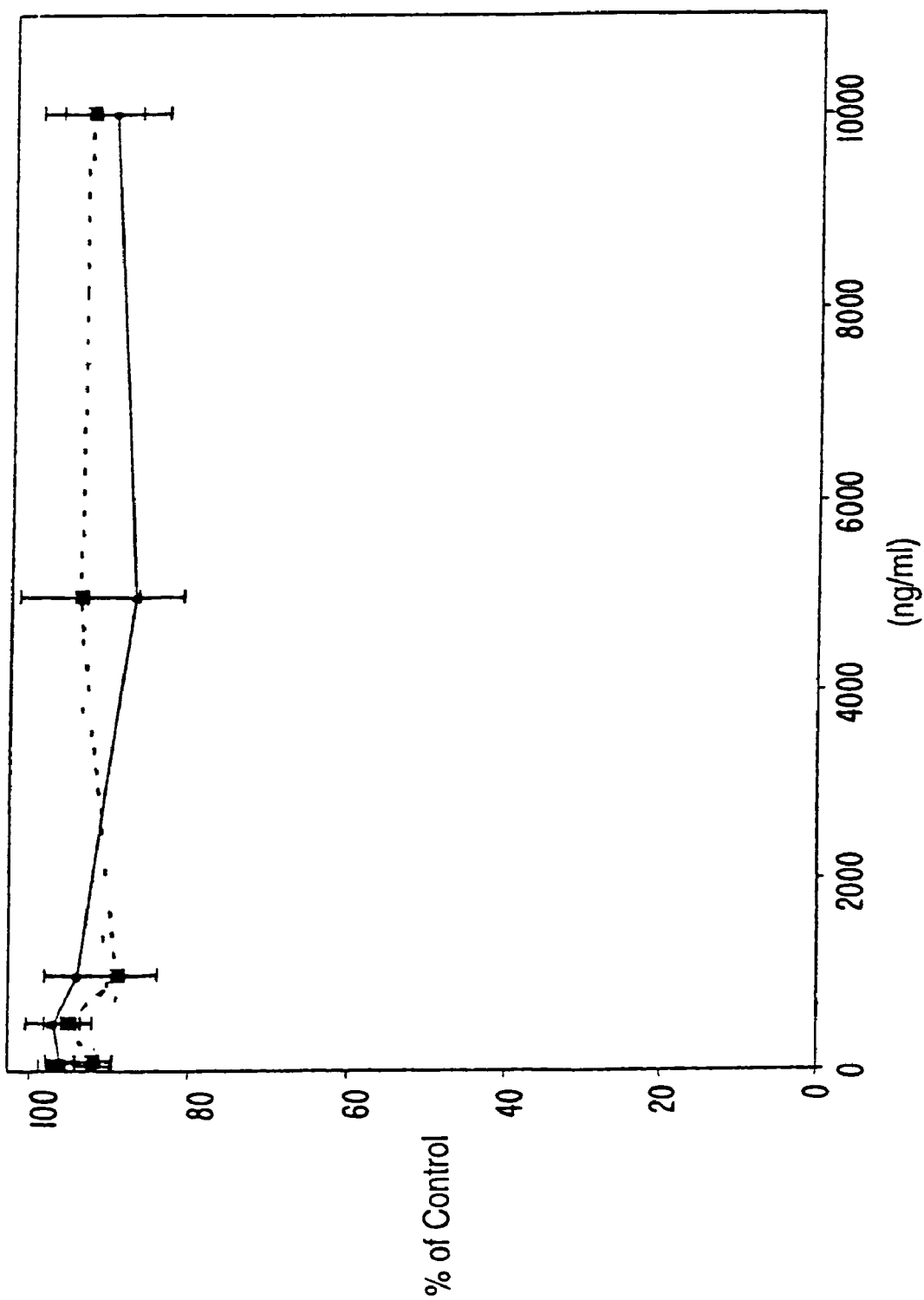

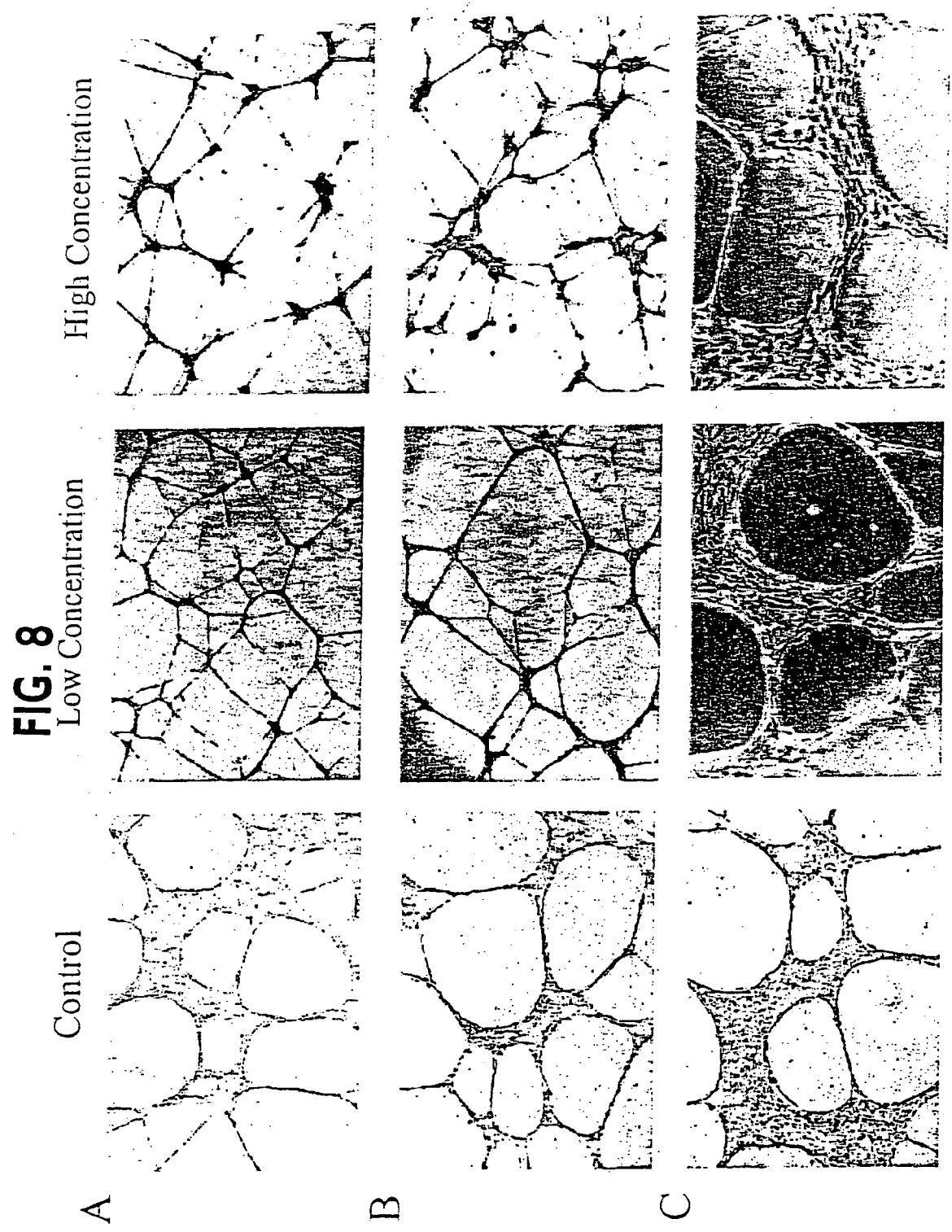

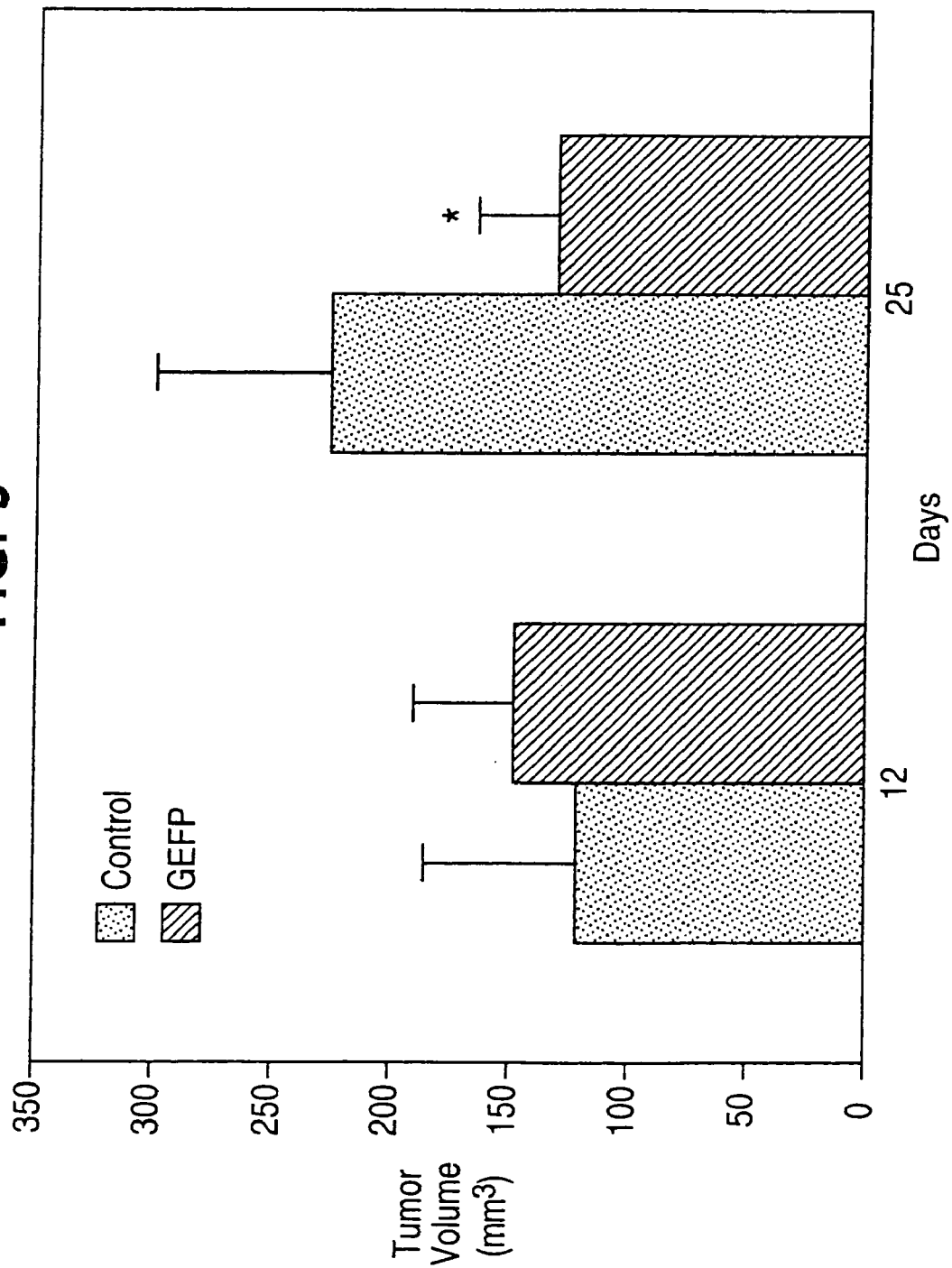

Preliminary in vivo studies of G129R-Endo (1)
(human breast cancer cell line, T-47D in nude mice)

Preliminary in vivo studies of G129R-Endo (2) (mouse breast cancer cell line, 4T1 in nude mice)

G129R-Angiostatin amino acid sequence FIG. 11A (G129R)  MLPICPGGAA RCQVTLRDLF DRAVVLSHYI HNLSSEMFSE FDKRYTHGRF ITKAINSCHT
SSLATPEDKE QAQQMNQKDF LSLIVSILRS WNEPLYHLVT EVRGMQEAPE AILSKAVEIE EQTKRLLEGM
ELIVSQVHPE TKENEIYPVW SGLPSLQMAD EESRLSAYYN LLHCLRRDSH KIDNYLKLLK CRIIHNNNC
GS (linker)
(Angio)  LFEKKVYLSE CKTGNGKNYR GTMSKTKNGI TCQKWSSTSP HRPRFSPATH PSEGLEENYC
RNPDNDPQGP WCYTTDPEKR YDYCDILECE EECMHCSGEN YDGKISKTMS GLECQAWDSQ SPHAHGYIPS
KFPNKNLKKN YCRNPDRELR PWCFTTDPNK RWELCDIPRC TTPPPSSGPT YQCLKGTGEN YRGNVAVTVS
GHTCQHWSAQ TPHTHNRTPE NFPCKNLDEN YCRNPDGKRA PWCHTTNSQV RWEYCKIPSC DSSPVSTEQL
APTAPPELTP VVQDCYHGDG QSYRGTSSTT TTGKKCQSWS SMTPHRHQKT PENYPNAGLT MNYCRNPDAD
KGPWCFTTDP SVRWEYCNLK KCSGTEASVV APPPVVLL

G129R-Flk-BP amino acid sequence FIG. 11B (G129R)  MLPICPGGAA RCQVTLRDLF DRAVVLSHYI HNLSSEMFSE FDKRYTHGRF ITKAINSCHT
SSLATPEDKE QAQQMNQKDF LSLIVSILRS WNEPLYHLVT EVRGMQEAPE AILSKAVEIE EQTKRLLEGM
ELIVSQVHPE TKENEIYPVW SGLPSLQMAD EESRLSAYYN LLHCLRRDSH KIDNYLKLLK CRIIHNNNC
GS (linker)
(Flk-BP)  ASVGLPSVSL DLPRLSIQKD ILTIKANTTL QITCRGQRDLD WLWPNNQSGS EQRVEVTECS
DGLFCKTLTI PKVIGNDTGA YKCFYRETDL ASVIYVYVQD YRSPFIASVS DQHGVVYITE NKNKTVVIPC
LGSISNLNVS LCARYPEKRF VPDGNRISWD SKKGFTIPSY MISYAGMVFC EAKINDESYQ SIMYIVVVVG
YRIYDVVLSP SHGIELSVGE KLVLNCTART ELNVGIDFNW EYPSSKHQHK KLVNRDLKTQ SGSEMKKFLS
TLTIDGVTRS DQGLYTCAAS SGLMTKKNST FVRVHEKPFV AFGSGMESLV EATVGERVRI PAKYLGYPPP
EIKWYKNGIP LESNHTIKAG HVLTIMEVSE RDTGNYTVIL TNPISKEKQS HVVSLVVYVP PQIGEKSLIS
PVDSYQYGTT QTLTCTVYAI PPPHHIHWYW QLEEECANEP SQAVSVTNPY PCEEWRSVED FQGGNKIEVN
KNQFALIEGK NKTVSTLVIQ AANVSALYKC EAVNKVGRGE RVISFHVTRG PEITLQPDMQ PTEQESVSLW
CTADRSTFEN LTWYKLGPQP LPIHVGELPT PVCKNLDTLW KLNATMF
SNSTNDILIMELKNASLQDQGDYVCLAQDRKTKKRHCVVRQLTVLERVAPTITGNLENQTTSIGESIEVSCTASGNP
PPQ
IMWFKDNETLVEDSGIVLKDGNRNLTIRRVRKEDEGLYTCQACSVLGCAKVEAFFIIEGAQEK

FIG. 12
A 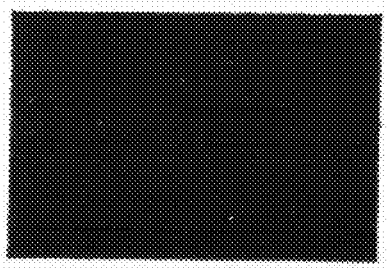 B 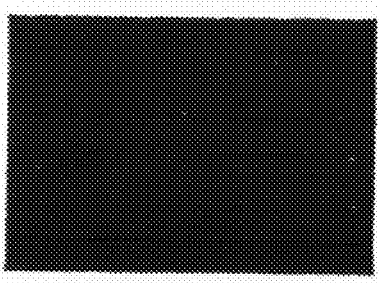
C 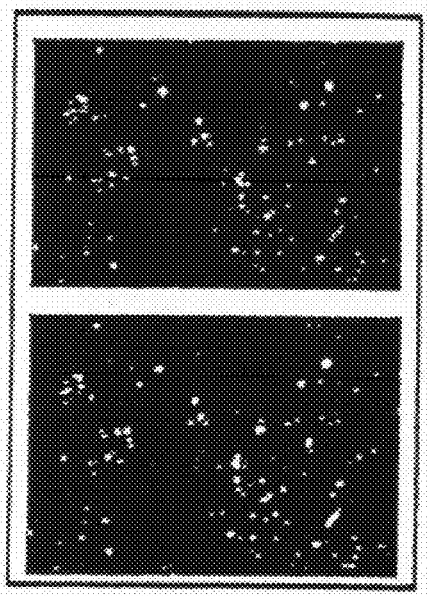 D 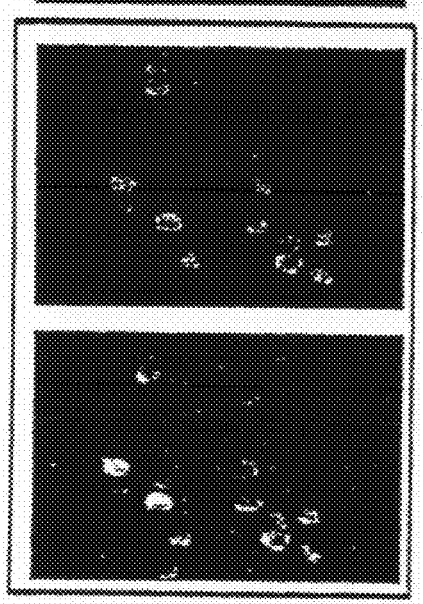
E 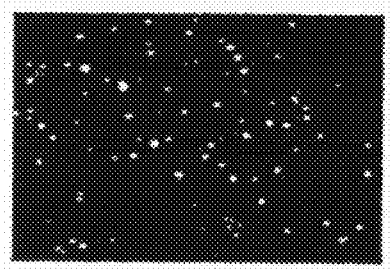 F 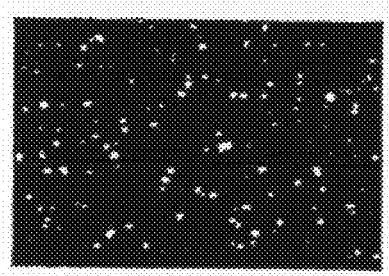
G 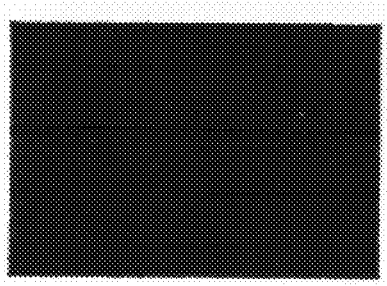 H 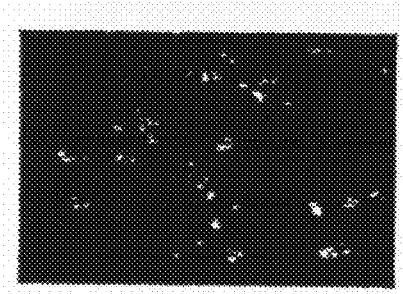

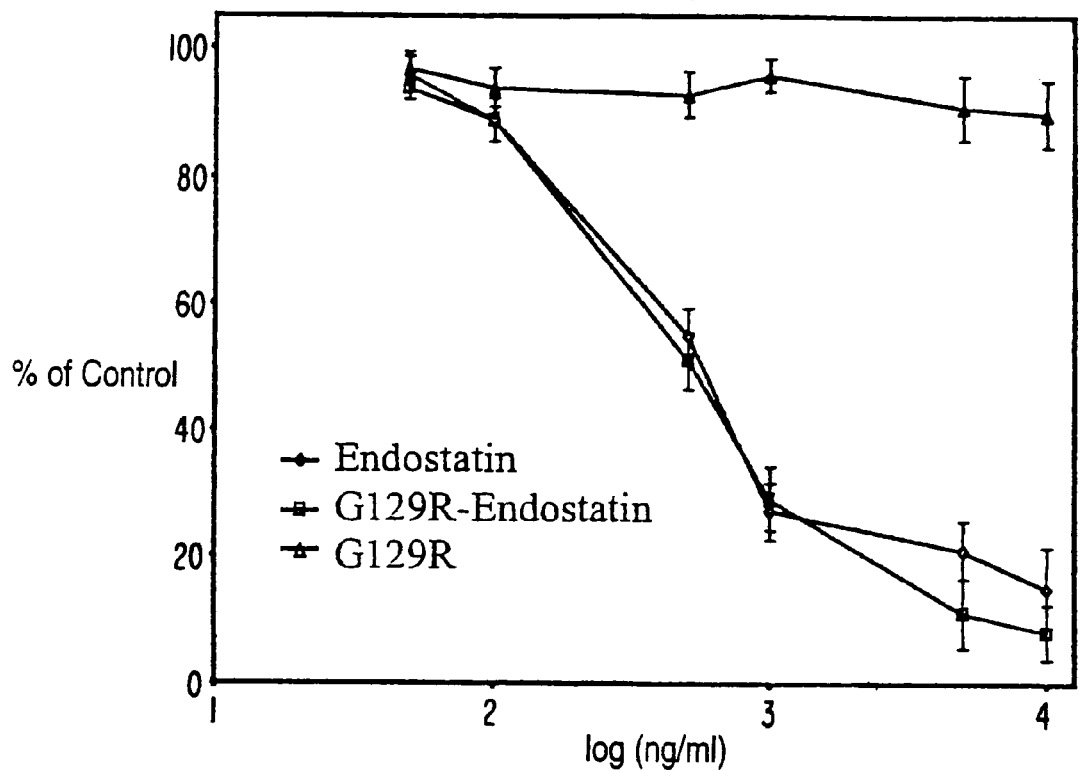
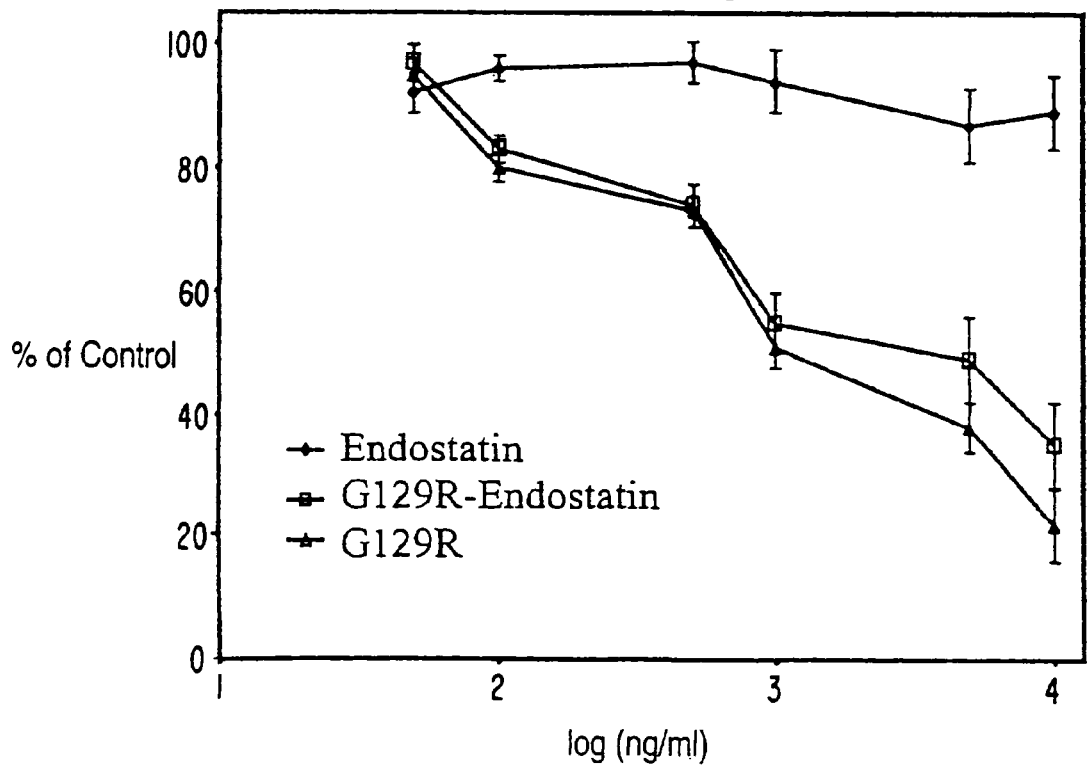

HUMAN PROLACTIN ANTAGONIST-ANGIOGENESIS INHIBITOR FUSION PROTEINS

STATEMENT REGARDING PRIORITY

This application is a divisional application of U.S. application Ser. No. 10/449,609, filed Jun. 6, 2003, now allowed, which claims priority to U.S. Provisional Application No. 60/384,121, filed May 31, 2002, both of which are incorporated herein by reference in their entirety.

STATEMENT REGARDING FEDERALLY SPONSORED RESEARCH OR DEVELOPMENT

The present invention was supported in part by the Endowment Fund of the Greenville Hospital System and Grants (DAMD17-99-1-9129, DAMD17-01-1-0207, NIH/NCI 1R21CA87093).

FIELD OF THE INVENTION

The present invention relates generally to the methodology of preparing and using fusion proteins comprising a human prolactin antagonist and an angiogenesis inhibitor for use in treatment of cancers.

BACKGROUND OF THE INVENTION

Human breast cancer is the predominant malignancy and the leading cause of cancer death in women from Western society, as reported by Miller et al., (eds) BIOLOGY OF FEMALE CANCERS, 31-42 (CRC Press, 1997). According to recent estimates from the American Cancer Society, one in every eight U.S. women will have breast cancer and the disease will kill 43,500 women in 1998.

Several lines of evidence have strongly linked prolactin (PRL) to breast cancer development. Expression levels of prolactin receptors (PRLR) reportedly are higher in human breast cancer cells than in normal breast epithelial cells (Reynolds et al., 1997), or in surgically removed breast cancer tissues (Touraine, Martini P. et al., *Increased Expression Of Prolactin Receptor Gene In Human Breast Tumors Versus Continguous Normal Breast Tissues*, (Abstract) 79th Annual Meeting of Endocrine Society, p. 113, (1997)). PRLR levels in malignant breast tissue can be five-fold higher than in the surrounding normal tissue (see Touraine et al. (1997), supra, making the malignant cells highly sensitive to the stimulation by hPRL. Additionally, it has been suggested that one mechanism of the mitogenic action of estrogen in breast may influence the production and secretion of human prolactin (hPRL), since there is a positive correlation between PRLR, estrogen receptors or progesterone receptor levels (Sirbasku, 1978; Dixon and Lippman 1986; Lippman and Dickson, 1989). Taken together, these findings lead to a hypothesis that hPRL serves as an autocrine/paracrine growth factor that plays an important role in mammary carcinogenesis (Clevenger, et al., *Am. J. Pathology*, 146: 695-705 (1995); Ginsburg, E. et al., *Cancer Res.*, 55: 2591-2595 (1995)).

An association between PRL expression and prostate disease has also been proposed in Wennbo et al., *Endocrinol.* 138: 4410-4415 (1997). PRL receptors are found in prostate tissue as reported Aragona et al., *Endocrinol.* 97: 677-684 (1975), and Leake et al., *J. Endocrinol.*, 99: 321-328 (1983). In addition, PRL levels has observed that can increase with age (Hammond et al., *Clin. Endocrinol.*, 7: 129-135 (1977), Vekemans et al., Br. Med. J. 4: 738-739 (1975)) coincident with the development of prostate hyperplasia. Transgenic mice overexpressing the PRL gene developed dramatic enlargement of the prostate gland. (see Wennbo et al. (1977), supra).

In view of its link to both breast and prostate cancer, PRL signaling represents an attractive target for therapeutic intervention. Heretofore, however, no suitable medicaments have been available for this purpose.

Inhibition of tumor angiogenesis has also been shown to hold great promise in treating cancer. Angiogenesis is a complex multi-step process that includes endothelial cell proliferation, migration, and differentiation, degradation of extracellular matrices, tube formation, and sprouting of new capillary branches (Tarui et al., 2001). Tumors often overexpress several pro-angiogenic molecules, including members of fibroblast growth factor (FGF) and vascular endothelial growth factor families (VEGF, Kim et al., 1993; Cheng et al., 1996; Benjamin and Keshet 1997). Both vessel density and angiogenesis directly correlate with metastasis formation and prognosis (Vijayagopal et al., 1998; Guidi et al., 2000). Excessive angiogenesis is part of the pathology of cancer, and preventing angiogenesis in a tumor could effectively induce a dormant state in the tumor cells (Folkman, 1995; Hanahan and Folkman 1996). Blocking angiogenesis has demonstrated great promise as a therapeutic approach to treat or even eradicate cancer by cutting off its blood supply. Anti-angiogenesis therapy for cancer is effective because: (1) tumor growth is dependent on angiogenesis; (2) degree of angiogenesis is proportional to invasiveness of tumor; (3) tumor endothelial cells are qualitatively different from endothelial cells in adult non-neoplastics tissue; (4) endogenous inhibitors and stimulators of angiogenesis exist and have been isolated. Ryan and Wilding 2000. A number of unique biological effects make the angiogenesis inhibitors intriguing anticancer agents such as (1) acquired drug resistance may be less likely than with cytotoxic agents; tumor dormancy may be achieved through prolonged drug administration; (2) haematological toxicity is unlikely as often seen in chemotherapeutics; and (3) potential for synergy with cytotoxic agents.

Two important molecules that have the most promising affect on inhibiting angiogenesis are the soluble endogenous factors angiostatin and endostatin. Endostatin, a 20 kDa C-terminal fragment of collagen XVIII, was first characterized by O'Reilly et al. (1997) and has been reported to exhibit antiangiogenic and tumor-regressing activities (O'Reilly et al., 1997; Boehm et al., 1997). Angiostatin, a proteolytic fragment of plasminogen, has also been described to exert potent antiangiogenic and anti-tumor activities in a variety of tumor models (O'Reilly et al., 1994, 1996). The mechanisms by which endostatin and angiostatin inhibit angiogenesis are not known. Both endostatin and angiostatin are currently in early phase of clinical trials (see review by Herbst et al., 2001).

One of the most potent and specific angiogenic factors is VEGF (reviewed by Ferrara, 2001). VEGF and its high-affinity tyrosine kinase receptor Flk-1/KDR are central regulators of both physiological and pathological angiogenesis. The high expression level of VEGF and Flk-1 in the tumor endothelium indicates that this signal transduction system stimulates the proliferation and the survival of tumor vessels by a paracrine mechanism (Kim et al., 1993; Cheng 1996; Ferrara, 2001). Direct evidence for this hypothesis was provided by the inhibition of tumor growth in animal models by the application of VEGF neutralizing antibodies (Kim et al., 1993; Cheng 1996) or by the gene transfer of dominant negative Flk-1 receptor mutants (Millauer et al., 1994; 1996). Flk-1 expression is suppressed in adult endothelium, but is highly induced in the newly formed blood vessels in a variety of human tumors. Most recent studies using adenovirus as a delivery system to directly compare the efficacy of endostatin, angiostatin as well ligand binding ectodomains of VEGF receptors Flk-1 (Flk-1-BP) show that Flk-1-BP is a better angiogenesis inhibitor than either endostatin or angiostatin (Kuo et al., 2001).

SUMMARY OF THE INVENTION

Accordingly, it is an object of the invention to provide a medicament that is capable of interfering with the prolactin signaling mechanism in a cancer cell.

It is yet another object of the invention to provide a medicament that inhibits angiogenesis in the tumor cell lines.

It is still another object of the invention to provide a method for treating a patient suffering from cancer by simultaneously antagonizing a receptor present in a targeted cancer cell and inhibiting tumor angiogenesis.

It is another object of the invention to provide a method of treating cancer by employing the medicaments described herein.

These and other objects which will be more readily apparent upon reading the following disclosure may be achieved by the present invention.

In a composition of matter aspect, the present invention relates substantially to a protein comprising a receptor antagonizing domain and an angiogenesis inhibiting domain. The invention further provides that the receptor antagonizing domain can be an apoptosis-promoting domain, while the angiogenesis inhibiting domain can be endostatin. The receptor antagonizing domain also can be the amino acid sequence SEQ ID NO: 1 or conservative variants thereof.

In a methodological aspect, the present invention relates to a method for treating cancer, comprising administering to a patient an effective amount of a protein having a receptor-antagonizing domain and angiogenesis inhibiting domain. The invention further provides a methodology for administering to a patient any of the proteins described herein.

BRIEF DESCRIPTION OF THE DRAWINGS

FIG. 1. Sequences of G129R, endostatin and G129R-endostatin (GEFP). DNA and protein sequences are given for G129R (SEQ ID NOS 2 & 1, respectively in order of appearance) (Panel A and B), endostatin (SEQ ID NOS 3 & 4, respectively in order of appearance) (Panel C and D) and G129R-endostatin fusion protein (GEFP) (SEQ ID NOS 5 & 6, respectively in order of appearance) (Panel E and F). The start codon, ATG and Met, is in bold for all sequences along with the mutation at amino acid position 129. The addition of a BamHI restriction site between G129R and endostatin resulted in two extra amino acid residues (Gly and Ser), indicated in bold. TAG is the stop codon.

FIG. 8. Analysis of endothelial tube formation. HUVEC's (25,000 cells/well) in EGM-2 medium without antibiotic were plated onto Matrigel basement membrane coated wells and evaluated for their ability to form tubal structures similar to that of blood vessels. Panel A represents the effect endostatin has on endothelial cells to form tubes. A low (100 ng/ml) and high (1000 ng/ml) concentration was performed for each experiment. Panel B represents GEFP treatment and Panel C represents the effect that G129R has on HUVEC tube formation. Each well was performed in triplicate and in a dose dependent manner. Control wells were performed with medium deficient of any treatment. Wells were viewed with a microscope and pictures were taken at 40× magnification and stained with diff-quik fixative.

FIG. 9. Preliminary analysis of human breast cancer inhibition in vivo. Eight athymic nude mice were inoculated s.c. T-47D cells mixed with Matrigel and the resulting tumors were allowed to grow for 21 days. Tumor volume was calculated on day 12 and day 25 post treatment using the equation:

[(short dimension$^2$)×(long dimension)]/2. Values are represented as means±SD for each group (n=3). *, P<0.05 versus control mice at 25 days post treatment.

FIG. 10. Preliminary studies of tumor growth inhibition in vivo with G129R-endostatin fusion proteins. (A) Four nude mice were inoculated s.c. T-47D human breast cancer cells mixed with Matrigel and the resulting tumors were allowed to grow for 21 days and (B) four nude mice were inoculated s.c. 4T1 mouse breast cancer cells mixed with Matrigel and the resulting tumors were allowed to grow for 7 days. Tumor volume was calculated at various times post treatment with G129R-endo fusion protein using the equation: [(short dimension$^2$)×(long dimension)]/2.

FIG. 11. Sequences of the prolactin antagonist-angiogenesis inhibitor fusion proteins. Amino acid sequences are given for (A) G129R-angiostatin (SEQ ID NO: 7) and (B) G129R-Flk1-bp (SEQ ID NO: 8) are depicted.

FIG. 12. Immunofluorescence staining of HUVEC and T-47D cells. Panel C(HUVEC's) and Panel D (T-47D) represent cells treated with G129R-Endostatin and stained with anti-human PRL and anti-human endostatin. Panels C and D are boxed to represent the same field of view. Both Panel E (HUVEC) and Panel F (T-47D) represent cells treated with endostatin and G129R and stained with anti-human endostatin. Both HUVEC (Panel G) and T-47D (Panel H) cells were treated with endostatin and G129R and stained with anti-human PRL. Negative controls of HUVEC and T-47D cells were presented as Panels A and B respectively. The secondary antibodies used were Alexa Fluor 594 goat anti-mouse IgG (red fluorescence, PRL) and Alexa Fluor 488 goat anti-rabbit IgG (green fluorescence, endostatin) respectively for each primary antibody. Pictures were taken digitally at 450× magnification.

FIG. 13. Breast cancer and endothelial cell proliferation assay. Purified human endostatin (solid ♦), G129R-Endostatin (□) and G129R (Δ) were tested for their anti-proliferative ability using HUVEC's (A) and T-47D cells (B). Viability of cells was determined by the colorimetric MTS-PMS assay (Promega). Data are represented by the percent of viable cells after treatments. Panel A, Ability of endostatin and G129R-Endostatin to inhibit bFGF-induced endothelial cell proliferation using G129R as the control. Panel B, Effects of G129R and G129R-Endostatin to inhibit the proliferation of human breast cancer cell line T-47D using endostatin as the control. Each experiment was carried out in triplicate and the data are represented as the mean±SE of three experiments.

Figure 14:
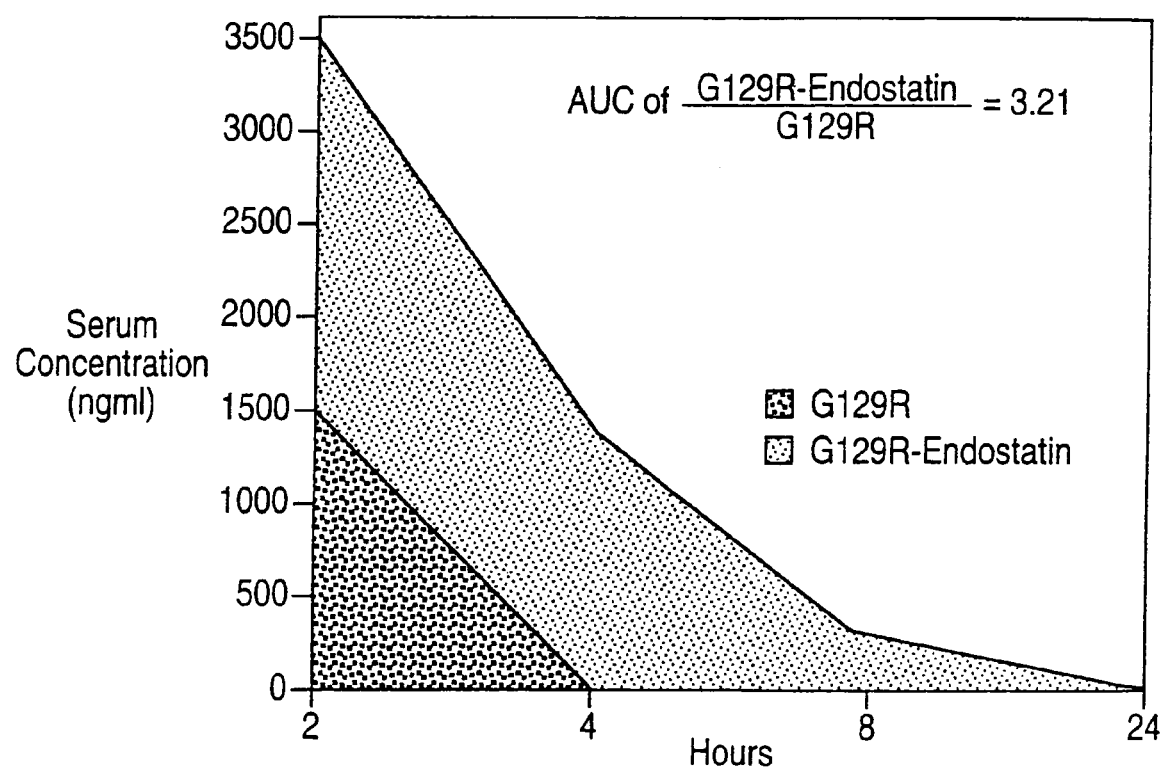

FIG. 14. Pharmacokinetic analysis of G129R-Endostatin in Balb/c mice. Female Balb/c mice (n=4) were injected i.p. with either G129R-Endostatin (200 μg) or G129R (200 μg) and serum samples were collected by bleeding via tail vein at the indicated time intervals. The serum concentration of both G129R and G129R-Endostatin was determined using the hPRL IRMA kit (DPC, Inc.).

FIG. 15. In vivo analysis of human breast cancer inhibition using G129R-Endostatin. Fifty athymic nude mice per group were inoculated (s.c.) with 5×10$^4$ 4T1 cells. Tumors were allowed to establish for 5 days. Mice were randomized and into 5 groups of ten and injected with G129R (2.5 mg/kg/mouse), endostatin (2.5 mg/kg/mouse), G129R-Endostatin (5 mg/kg/mouse), the combination of G129R (2.5 mg/kg/mouse) and endostatin (2.5 mg/kg/mouse), or 100 μl of sterile PBS for 35 consecutive days. Panel A, Tumor volume was determined every 5 days post treatment by measuring the short axis (S) and the long axis (L) of the tumors and calculated using the equation: [(S)$^2$×L]/2. Panel B, once the final tumor volume was measured the tumors were removed and weighed. Values are represented as mean±SE for each group (n=10). *, represents treatments that are significant (P<0.05) to that of the control. **, represents treatments that are significant (P<0.05) to all other treatments including the control.

DETAILED DESCRIPTION OF THE PREFERRED EMBODIMENTS

It has been discovered by the present inventors that the combined effects of endocrine-based and targeted anti-angiogenesis therapies greatly enhance the treatment of cancer. For instance, compositions and methods of treatment disclosed herein act to inhibit the autocrine/paracrine effects of endogenous PRL by blocking the PRLR, typically resulting in apoptosis. In addition, this approach inhibits tumor angiogenesis, further inhibiting tumor growth.

As used herein, "apoptosis" refers to a process whereby developmental or environmental stimuli activate a genetic program to implement a specific series of events that culminate in the death and efficient disposal of a cell. The morphological changes in the cell include dramatic shrinkage of cell volume, accompanied by dilation of endoplasmic reticulum and convolution of the plasma membrane. In turn, this causes the cell to break up into a series of membrane-bounded bodies, containing structurally normal, yet compacted, organelles. The nucleus undergoes discontinuous chromatin condensation and nuclease-mediated DNA fragmentation occurs, degrading chromosomal DNA into small oligonucleosomal fragments. The nucleus and cytoplasm condense and the dying cell ultimately fragments into membrane-bound apoptotic bodies that are rapidly phagocytosed and digested by macrophages or by neighboring cells.

The present invention combines the benefits associated with blocking the PRLR and inhibiting angiogenesis by utilizing a multi-domain molecule, each domain having the ability to carry out one of these functions. Typical molecules have a "receptor-antagonizing domain" or an "apoptosis-promoting domain," combined with a "angiogensis inhibiting domain."

Since drug efficacy is affected by its serum half-life, one potential limitation of G129R alone, as well as endostatin alone in cancer treatment is their relative short serum half-life (Zhang et al., *Clin. Cancer Res.*, 8:1196-1205 (2002)). The present in this study demonstrates that G129R-Endostatin has a three-fold longer serum half-life when compared to G129R alone While not wishing to be bound to a particular theory, the inventors believe that the enhanced in vivo anti-tumor effects of G129R-Endostatin, as compared to G129R and endostatin may also be attributed to the localization of endostatin portion of the fusion protein to the tumor site. The localized endostatin, in turn, results in inhibition of the surrounding endothelial cells that will form the tumor associated vascular network, and inhibition of breast cancer cell proliferation within the tumor mass.

As used herein, a "receptor-antagonizing domain" is a ligand that specifically binds to a receptor that is associated with a disorder like cancer, whereupon binding to the receptor, the receptor-antagonizing domain acts to inhibit one or more cellular processes, thereby interrupting the etiology or maintenance of the disease. Such a domain that induces apoptosis is herein referred to as the "apoptosis-promoting domain," while a "angiogenesis inhibiting domain" is one that inhibits formation of the tumor neovasculature.

The benefits of a fusion protein having these characteristics are immense. For example, carcinogenic tissues are often characterized by increased levels of one or more protein receptors. A fusion protein containing a domain that is specific to one of these receptors will be able to specifically target the cancer tissue. Where the receptor antagonizing domain disrupts the etiology of the cancer, or disrupts cancer maintenance, as is the case of an apoptosis-promoting domain, the receptor antagonizing portion of the molecule has a direct therapeutic effect. In addition, due to the presence of the angiogenesis inhibiting domain, the molecule has a secondary therapeutic effect by inhibiting formation of the tumor neovasculature, thereby depriving the tumor of blood supply and the associated nutrients needed for tumor growth.

Accordingly, candidates to receive the therapy according to this invention include individuals who suffer from malignant tumors those of which are characterized by the presence of at least one receptor related to tumor maintenance or proliferation. In a preferred embodiment, the receptor-antagonizing domain of the fusion protein is an apoptosis-promoting domain, which binds to a targeted membrane-bound receptor. Such binding induces apoptosis; simultaneously, the angiogenesis inhibiting domain inhibits formation of the tumor neovasculature.

The Inventive Bi-Functional Protein:

In accordance with the invention, bi-functional proteins are contemplated that have unique dual therapeutic effects on malignant tissue, namely (a) receptor-antagonizing and/or apoptosis-promoting (which may be one and the same) and (b) angiogenesis inhibition. The invention also contemplates nucleic acids (e.g. DNA or RNA) encoding the inventive bi-functional proteins.

Receptor-Antagonizing Domain

The invention contemplates a first domain that, in one aspect, will localize the effects of the receptor antagonizing domain to the diseased tissue. For example, carcinogenic tissues are often characterized by increased levels of one or more protein receptors. A fusion protein containing a domain that is specific to one of these receptors will be able to specifically target the cancer tissue, resulting in a localized tumor cytotoxicity reaction directed to the targeted tissue.

In one embodiment, the domain that targets a particular receptor site is a receptor-antagonizing domain, which, as its name suggests, binds to and antagonizes its cognate receptor. As long as the receptor antagonizing domain recognizes a receptor that is highly expressed in cancer cells, it is suitable for use in the present invention. In a preferred embodiment, the receptor-antagonizing domain is an apoptosis-promoting domain.

An additional therapeutic benefit of this dual-function molecule is that the receptor-antagonizing domain typically has endocrine-blocking ability. Thus, where the receptor-antagonizing domain, for example, is a prolactin antagonist, the normal endocrine function of prolactin will be disrupted. As a consequence of this endocrine-blocking, in the case of prolactin and similar molecules, for instance, apoptosis of the targeted cells can result. In that case, the receptor-antagonizing domain is also an apoptosis-promoting domain.

In the case of an apoptosis-promoting domain, such a domain generally is designed by creating antagonists of the normal function of a cellular component that is involved in preventing apoptosis. In both breast and prostate cancer tissue, for example, carcinogenesis and malignant cell proliferation is stimulated, at least in part, by increased levels of PRLR. Signaling via the PRLR is known to be mediated by dimerization of the prolactin receptor, which is itself mediated by binding of receptor-bound prolactin molecules. The binding of endogenous PRL to two PRLRs induces PRLR dimerization, thereby triggering signal transduction into the cancer cells. Accordingly, one embodiment of the invention entails antagonizing the normal apoptosis-inhibiting function of prolactin using a prolactin antagonist (PRLA) (i.e., a prolactin antagonist domain).

Signal transduction in the PRLR signaling pathway involves signal transducers and activators of transcription (STAT) phosphorylation, which is involved in preventing or blocking apoptosis, the normal result of PRLR agonism. Thus, G129R antagonist promotes apoptosis by inhibiting STAT 5 phosphorylation in human breast cancer cells. Accordingly, blocking the PRLR inhibits the autocrine/paracrine effects of endogenous PRL, which involves STAT 5, and results in apoptosis. Thus, one class of apoptosis-promoting compounds contemplated by the invention is one that can inhibit STAT 5 phosphorylation.

A suitable PRLA contemplated by the invention generally will retain the characteristic of specific binding to the PRLR, yet will have some structural deficiency that disrupts the normal PRL apoptosis-blocking mechanism. Such a structural deficiency includes those that disrupt PRL (and thus PRLR) dimerization.

Figure 3:
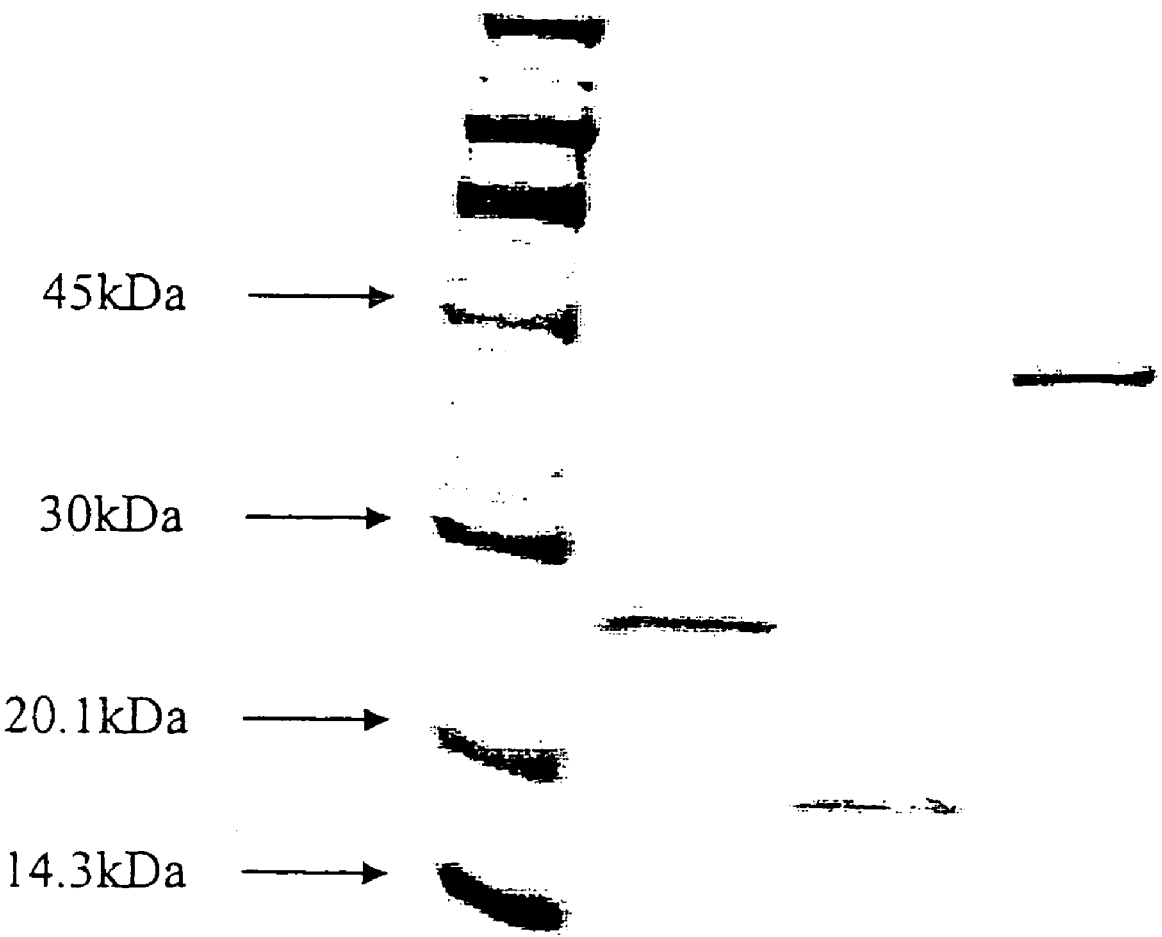
FIG. 3. Determination of fusion protein size. One microgram of purified G129R (Lane 1), endostatin (Lane 2) and GEFP (Lane 3) were run on a 12% SDS-PAGE gel and stained with Coomassie Blue. Lane M represents protein markers with their respective sizes indicated. G129R migrates at 23 kDa (lane 1) and endostatin at approximately 20 kDa (lane 2). G129R-Endostatin migrated at approximately 43 kDa (lane 3).
Figure 4:
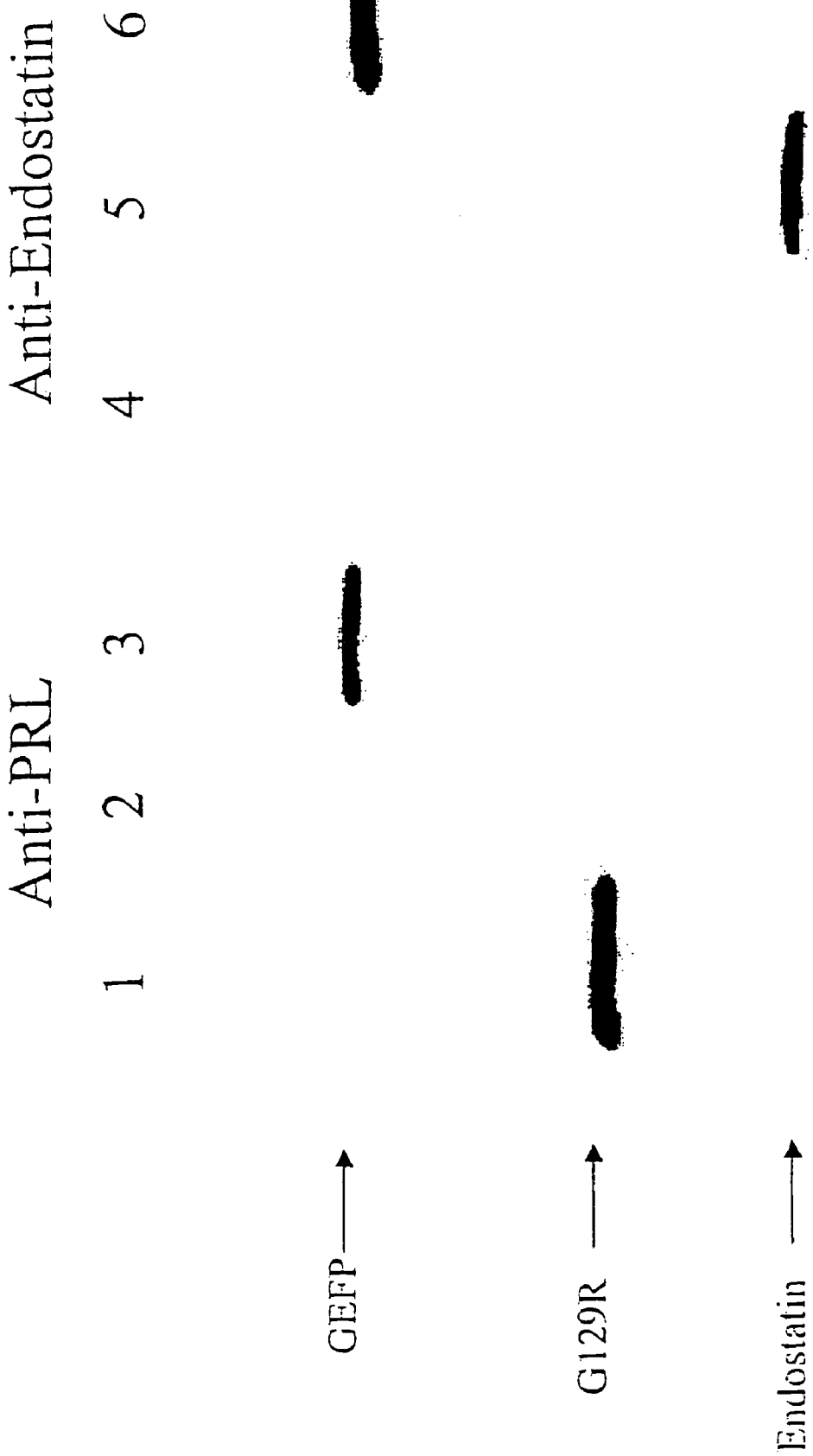
FIG. 4. Immunoblot analysis for GEFP. All lanes were run with 10 ng of G129R (Lane 1 and 4), endostatin (Lane 2 and 5) and GEFP (Lane 3 and 6) on a 12% SDS-PAGE gel. Lanes 1-3 were incubated with a polyclonal rabbit anti-hPRL antibody and Lanes 4-6 were incubated with a polyclonal rabbit anti-endostatin antibody. A goat anti-Rabbit IgG horseradish peroxidase conjugate was used as secondary antibody and detected with ECL.
Figure 5:
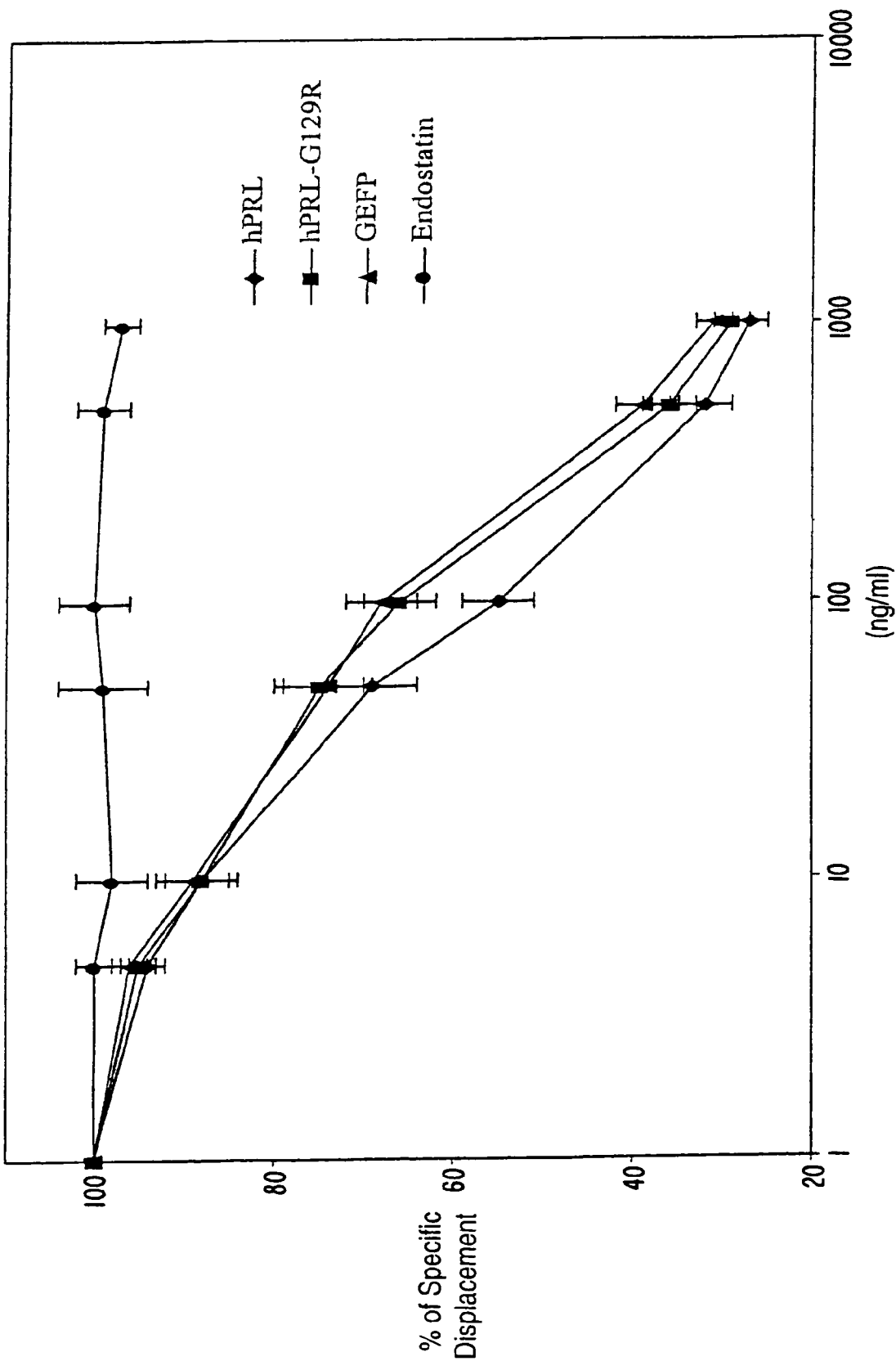
FIG. 5. Competitive radioreceptor binding assays. The concentrations of the respective treatments are given on a log scale. The values are represented as the percentage of the displacement of the total binding of each protein to human breast cancer cell line T-47D. The data is presented from triplicate experiments and is represented as the means±SD.

In one preferred embodiment, shown in SEQ ID NO: 1, this structural deficiency is a substitution of Gly to Arg at a position corresponding to 129 in hPRL (denoted as hPRL-G129R). As shown in FIG. 3, a fusion protein incorporating the G129R mutation is recognized by and anti-hPRL antibody. The K data presented FIGS. 4-6 demonstrate that this mutated hPRL acts as a true hPRLR antagonist. Accordingly, a receptor-antagonizing domain such as hPRL-G129R can serve as a therapeutic medicament for treating certain types of cancer.

This embodiment is supported by Chen et al., *Clin. Can. Res.* 5: 3583-93 (1999), who disclose a species comparison of amino acid sequences within the third α-helical region of PRLs, shown in Table 1. (SEQ ID NOS 9-40, respectively, in order of appearance)

TABLE 1*

| Species | Domain | Peptide Sequence | | Pep. Seq. |
|---|---|---|---|---|
| | | | 129 | |
| Human | PRL | IEEQTKRLLR | G | MELIVS-QVHP |
| Rat | PRL | IEEQNKRLLE | G | IEKIIG-QAYP |
| Mouse | PRL | IEEQNKQLLE | G | VEKIIS-QAYP |
| Hamster | PRL | IGEQNKRLLE | G | IEKILG-QAYP |
| Fin whale | PRL | EEEENKRLLE | G | MEKIVG-QVHP |
| Mink | PRL | IEEENRRLLE | G | MEKIVG-QVHP |
| Cattle | PRL | IEEQNKRLIE | G | MEMIFG-QVIP |
| Sheep | PRL | EEEENKRLLE | G | MENIFG-QVIP |
| Pig | PRL | IEEQNKRLLE | G | MEKIVG-QVHP |
| Camel | PRL | IEEQNKRLLE | G | MEKIVG-QVHP |
| Horse | PRL | EIEQNRRLLE | G | MEKIVG-QVQP |
| Elephant | PRL | VKEENQRLLE | G | IEKIVD-QVHP |
| Ancestral mammal | PRL | IEEENKRLLE | G | MEKIVG-QVHP |
| Chicken | PRL | IEEQNKRLLE | G | MEKIVG-RVHS |
| Turkey | PRL | IEEQDKRLLE | G | MEKIVG-RIHS |
| Sea turtle | PRL | IEEQNKRLLE | G | MEKIVG-QVHP |

TABLE 1*-continued

| Species | Domain | Peptide Sequence | | Pep. Seq. |
|---|---|---|---|---|
| Crocodile | PRL | IEEQNKRLLE | G | MEKIIG-RVQP |
| Alligator | PRL | IEEQNKRLLE | G | MEKVIG-RVQP |
| Ancestral amniote | PRL | IEEQNKRLLE | G | MEKIVG-QVHP |
| Xenopus | PRL | VEEQNKRLLE | G | MEKIVG-RIHP |
| Bullfrog | PRL | VEEQTKRLLE | G | MERIIG-RIQP |
| Lungfish | PRL | VEDQTKQLIE | G | MEKILS-RMHP |
| Tilapia | PRL | MQQYSKSLKD | G | LD-VLSSKMGS |
| Tilapia | PRL | MQEHSKDLKD | G | LD-ILSSKMGP |
| Common carp | PRL | LQENINSLGA | G | LEHVF-NKMDS |
| Bighead carp | PRL | LQDNINSLGA | G | LERVV-HKMGS |
| Silver carp | PRL | LQDNINSLVP | G | LEHVV-HKMGS |
| Chun salmon | PRL | LQDYSKSLGD | G | LD-IMVNKMGP |
| Chinook salmon | PRL | LQDYSKSLGD | Q | LD-IMVNKMGP |
| Trout | PRL | LQDYSKSLGD | G | LD-IMVNKMGP |
| | | 120 | | |
| Human | GH | VYDLLKDLEE | G | IQTLMRELEDG |
| Bovine | GH | VYEKLKDLEE | G | ILALMRELEDG |

*Table 1 This table has been reproduced from Cooke et al. Journal of Biological Chemistry, 256: 4007-4016 (1981). We note that this table provides that the amino acid in position number 128 of the human prolactin sequence is an arginine. However, our sequence data (see FIG. 1) and Genebank accession numbers BC015850, NM_00948, X54393, V00566, M29386, D00411 and U75583 indicate that amino acid number 128 in hPRL is a glutamic acid.

According to Table 1, it is clear that Gly 129 of hPRL is invariable among PRLs, suggesting an important role in its function. Thus, substituting any amino acid for Gly 129 should produce PRLA in each of these species (Chen et al., *Molec. Endocrinol.* (1995)). In one embodiment, an antagonist is created by substituting a relatively bulky side chain amino acid, such as Arg for Gly 129. Accordingly, one aspect of the invention contemplates conservative variants of PRL that are characterized by the presence of a relatively small side-chain amino acid (i.e. Gly) at a specific position, such that substituting the small side-chain amino acid for a bulky side-chain amino acid will result in an antagonistic form of the protein. In a preferred embodiment, the receptor antagonizing domain is a hPRL-G129R antagonist.

The receptor-antagonizing domain of present invention also includes conservative variants of receptor antagonizing domains discussed herein. The overall structure and composition of the inventive domains, in that respect, are important only insofar as they confer the appropriate functional characteristics, i.e., receptor antagonism, apoptosis induction, positive immunomodulation.

Conservative variants according to the invention generally conserve the overall molecular structure of the protein domains. Given the properties of the individual amino acids comprising the disclosed protein products, some rational substitutions will be apparent. Amino acid substitutions, i.e. "conservative substitutions," may be made, for instance, on the basis of similarity in polarity, charge, solubility, hydrophobicity, hydrophilicity, and/or the amphipathic nature of the residues involved.

For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Conservative variants specifically contemplate truncations of the presently described receptor antagonizing domains. Truncations may be made from the N- or C-terminus, but generally do not entail deleting more than about 30% of the native molecule. More preferably, less than about 20%, and most preferably, less than about 10%, of the native molecule is deleted.

In general, both the DNA and protein molecules of the invention can be defined with reference to "sequence identity." Some molecules have at least about 50%, 55% or 60% identity. Preferred molecules are those having at least about 65% sequence identity, more preferably at least 70% sequence identity. Other preferred molecules have at least about 80%, more preferably at least 85%, sequence identity. Most preferred molecules have at least about 90%, more preferably at least 95%, sequence identity. As used herein, two nucleic acid molecules or proteins are said to "share significant sequence identity" if the two contain regions which possess greater than 85% sequence (amino acid or nucleic acid) identity.

"Sequence identity" is defined herein with reference the Blast 2 algorithm, which is available at the NCBI using default parameters. References pertaining to this algorithm include: those found at Altschul, S. F., Gish, W., Miller, W., Myers, E. W. & Lipman, D. J. (1990) "Basic local alignment search tool" J. Mol. Biol. 215: 403-410; Gish, W. & States, D. J. (1993) "Identification of protein coding regions by database similarity search." Nature Genet. 3: 266-272; Madden, T. L., Tatusov, R. L. & Zhang, J. (1996) "Applications of network BLAST server" Meth. Enzymol. 266: 131-141; Altschul, S. F., Madden, T. L., Schaffer, A. A., Zhang, J., Zhang, Z., Miller, W. & Lipman, D. J. (1997) "Gapped BLAST and PSI-BLAST: a new generation of protein database search programs." Nucleic Acids Res. 25: 3389-3402; and Zhang, J. & Madden, T. L. (1997) "PowerBLAST: A new network BLAST application for interactive or automated sequence analysis and annotation." Genome Res. 7: 649-656. Accordingly, the prolactin peptide sequences from different species, which include those listed in Table 1, can be aligned, using standard computer programs like BLAST, to inform further variation in prolactin-derived receptor-antagonizing domains that preserve their essential function.

In addition to proteins that are conservative variants of those disclosed herein, the invention also contemplates the use of proteins that play a role in inducing tumor proliferation, wherein an amino acid substitution will inhibit the protein's ability to induce this proliferation. For example, Gly 119 and Gly 120 of bovine growth hormone (bGH) and hGH, respectively, play critical roles in the action of GH in stimulating growth enhancement. Growth hormone receptor (GHR) dimerization is thought to be a key step for HG signal transduction. Accordingly, any amino acid substitution (other than Ala), especially one with a bulky side chain such as Arg at these respective positions will prevent receptor dimerization, resulting in a growth hormone antagonist (GHA). Thus, antagonists such as GHA are contemplated by the invention. In a preferred embodiment, the receptor antagonizing domain is a hGH-G120R antagonist.

Angiogenesis Inhibiting Domain.

The invention also contemplates an additional, yet separate, domain that acts as an angiogenesis inhibitor. Preferred angiogenesis inhibiting domains include endostatin. In addition to endostatin, the invention contemplates other molecules, including proteins, that are capable of inhibiting the formation of the tumor neovasculature. For example, endostatin, angiostatin, and Flk-1 bp are contemplated in the present invention.

Flk-1 is a full length receptor that binds VEGF. Flk-1 bp is the extracellular portion of the Flk-1 receptor that is responsible for binding to VEGF. Flk-1 bp instead of Flk-1 is used in the present invention in order to avoid insertion into the cell membrane.

The invention also includes conservative variants (as detailed above) of the aforementioned angiogenesis inhibiting domains.

Preparing Exemplary Bi-Functional Molecules:

A bi-functional protein contemplated by this invention is one that contains each of the previously mentioned domains, namely receptor-antagonizing (which also may be apoptosis-promoting) and angiogenesis inhibiting, wherein upon such fusing, both domains substantially retain their associated characteristics, independent of the other. FIG. 1 discloses one embodiment of the invention, according to these characteristics. Although typically produced as fusion proteins, the domains also may be fused by conventional chemical means, using multifunctional cross-linkers, for example. When fusion proteins are made, either domain may be placed C-terminal or N-terminal to the other.

Figure 2:
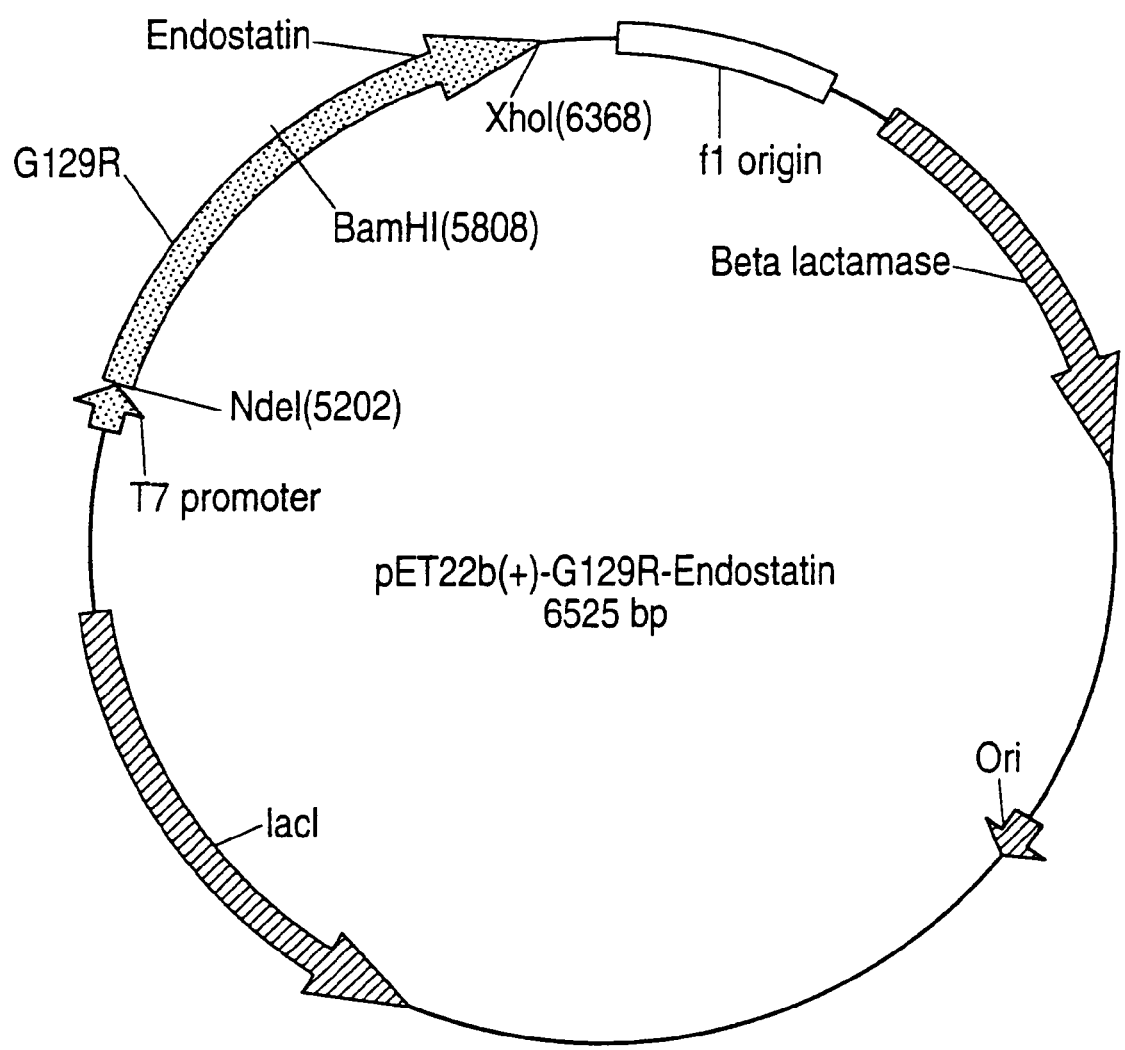
FIG. 2. Cloning and construction of the expression plasmid for GEFP production. Endostatin was amplified from a human liver cDNA library using PCR. This was ligated, with PCR fragment amplified from G129R, into an *E. coli* expression vector, pET22b(+), at the NdeI and XhoI sites. A BamHI restriction site was incorporated between G129R and endostatin for cloning purposes.

In one embodiment, the fusion protein is a hPRLA-endostatin protein, as shown in FIG. 1. This fusion protein can be integrated into an expression vector, as shown in example 1 and FIG. 2. The generated expression vector can then be transfected into a stable cell line to subsequently produce a purified protein. Examples 2 and 3 are non-limiting procedures for carrying out the vector transformation and purification processes. This fusion protein has the C-terminus of PRLA fused to the N-terminal side of endostatin, which is shown in FIG. 1. However, the invention also contemplates any fusion protein having domains as described herein.

Suitable methods for creating the fusion protein should be ones that do not substantially change the biological activity of either of these domains. For example, it has been demonstrated that fusion of the N-terminal of IL-2 to the C-terminal end of an antibody does not change the biological activity of IL-2 Reisfeld et al. (1996), supra. Therefore, a similar strategy can be adopted to produce a fusion protein according to the invention. This process includes designing a cDNA encoding a fusion protein which links the N-terminus of the positive immunomodulator domain to the C-terminus of receptor-antagonizing domain.

Moreover, there is evidence that the C-terminal ends of hGH (we deleted up to 10 amino acids) are not important for growth promoting activities in transgenic mice (Chen et al., 1993) and, based on structural similarity, fusion of a positive modulator to the C-terminal end of other receptor-antagonizing domains, such as hPRLA, should not alter the binding affinity of these domains.

The present invention is not limited to any particular method of producing the desired fusion protein contemplated herein. According to the contemplated recombinant methods of production, however, the invention provides recombinant DNA constructs comprising one or more of the nucleotide sequences of the domains described in the present invention. The recombinant constructs of the present invention comprise a vector, such as a plasmid or viral vector, into which a DNA or DNA fragment, typically bearing an open reading frame, is inserted, in either orientation. The invention further contemplates cells containing these vectors.

Recombinant protein production is well known in the art and is outlined briefly below.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may, also be employed as a matter of choice. In a preferred embodiment, the prokaryotic host is *E. coli*.

Bacterial vectors may be, for example, bacteriophage-, plasmid- or cosmid-based. These vectors can comprise a selectable marker and bacterial origin of replication derived from commercially available plasmids typically containing elements of the well known cloning vector pBR322 (ATCC 37017). Such commercial vectors include, for example, GEM 1 (Promega Biotec, Madison, Wis., USA), pBs, phagescript, PsiX174, pBluescript SK, pBs KS, pNH8a, pNH16a, pNH18a, pNH46a (Stratagene); pTrc99A, pKK223-3, pKK233-3, pKK232-8, pDR540, and pRIT5 (Pharmacia). A preferred vector according to the invention is the Pt71 expression vector (Paris et al., *Biotechnol. Appl. Biochem.* 12: 436-449 (1990)).

These "backbone" sections are combined with an appropriate promoter and the structural sequence to be expressed. Bacterial promoters include lac, T3, T7, lambda $P_R$ or $P_L$, trp, and ara. T7 is the preferred bacterial promoter.

Following transformation of a suitable host strain and growth of the host strain to an appropriate cell density, the selected promoter is derepressed/induced by appropriate means (e.g., temperature shift or chemical induction) and cells are cultured for an additional period. Cells are typically harvested by centrifugation, disrupted by physical or chemical means, and the resulting crude extract retained for further purification.

Eukaryotic Expression

Various mammalian cell culture systems can also be employed to express recombinant protein. Examples of mammalian expression systems include selected mouse L cells, such as thymidine kinase-negative (TK) and adenine phosphoribosul transferase-negative (APRT) cells. Other examples include the COS-7 lines of monkey kidney fibroblasts, described by Gluzman, *Cell* 23: 175 (1981), and other cell lines capable of expressing a compatible vector, for example, the C127, 3T3, CHO, HeLa and BHK cell lines.

Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 viral genome, for example, SV40 origin, early promoter, enhancer, splice, and polyadenylation sites may be used to provide the required non-transcribed genetic elements.

Mammalian promoters include CMV immediate early, HSV thymidine kinase, early and late SV40, LTRs from retrovirus, and mouse metallothionein-I. Exemplary mammalian vectors include pWLneo, pSV2cat, pOG44, pXT1, pSG (Stratagene) pSVK3, pBPV, pMSG, and pSVL (Pharmacia). In a preferred embodiment, the mammalian expression vector is pUCIG-MET. Selectable markers include CAT (chloramphenicol transferase).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a target protein in infected hosts. (E.g., See Logan et al., 1984, *Proc. Natl. Acad. Sci. USA* 81: 3655-3659).

Therapeutic Compositions:

The proteins of the present invention can be formulated according to known methods to prepare pharmaceutically useful compositions, whereby the inventive molecules, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A., Ed., Mack, Easton Pa. (1980)). To form a pharmaceutically acceptable composition suitable for effective administration, such compositions will contain an effective amount of one or more of the proteins of the present invention, together with a suitable amount of carrier vehicle.

Pharmaceutical compositions for use in accordance with the present invention may be formulated in conventional manner using one or more physiologically acceptable carriers or excipients. Thus, the bi-functional molecules and their physiologically acceptable salts and solvate may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they maybe presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the composition may take the form of tablets or lozenges formulated in conventional manner.

For administration by inhalation, the bi-functional molecules for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The bi-functional proteins may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the bi-functional molecules may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The compositions, since they are useful in cancer treatment, may be formulated in conjunction with conventional chemotherapeutic agents. Conventional chemotherapeutic agents include alkylating agents, antimetabolites, various natural products (e.g., vinca alkaloids, epipodophyllotoxins, antibiotics, and amino acid-depleting enzymes), hormones and hormone antagonists. Specific classes of agents include nitrogen mustards, alkyl sulfonates, nitrosoureas, triazenes, folic acid analogues, pyrimidine analogues, purine analogs, platinum complexes, adrenocortical suppressants, adrenocorticosteroids, progestins, estrogens, antiestrogens and androgens. Some exemplary compounds include cyclophosphamide, chlorambucil, methotrexate, fluorouracil, cytarabine, thioguanine, vinblastine, vincristine, doxorubincin, daunorubicin, mitomycin, cisplatin, hydroxyurea, prednisone, hydroxyprogesterone caproate, medroxyprogesterone, megestrol acetate, diethyl stilbestrol, ethinyl estradiol, tomoxifen, testosterone propionate and fluoxymesterone. In treating breast cancer, for example, tamoxifen is particularly preferred.

Methods of the Invention:

Treatment Methods

The inventive therapeutic methods according to the invention generally utilize the bi-functional proteins identified above. The domains of the fusion proteins share the ability to specifically target a specific tissue and/or augment an immune response to targeted tissue. Accordingly, a typical method, involves binding a receptor of a target cell by the receptor-antagonizing domain of the fusion protein and/or inhibiting formation of tumor neovasculature via the angiogenesis inhibiting domain.

For example, the instant invention describes that a novel fusion protein, such as GEFP, is able to bind to the PRL receptor (PRLR) on T-47D human breast cancer cells, for example, and inhibit the signal transduction induced by PRL. At the same time, GEFP is able to inhibit human umbilical vein endothelial cell (HUVEC) proliferation and disrupt the formation of endothelial tube structures with potency similar to that of endostatin. Therapeutic methods involve administering to a subject in need of treatment a therapeutically effective amount of a fusion protein. "Therapeutically effective" is employed here to denote the amount of fusion proteins that are of sufficient quantity to inhibit or reverse cancer growth (e.g., induce apoptosis). Some methods contemplate combination therapy with known cancer medicaments or therapies, for example, chemotherapy (preferably using compounds of the sort listed above) or radiation. The patient may be a human or non-human animal. A patient typically will be in need of treatment when suffering from a cancer characterized by increased levels of receptors that promote cancer maintenance or proliferation.

Administration during in vivo treatment may be by any number of routes, including parenteral and oral, but preferably parenteral. Intracapsular, intravenous, intrathecal, and intraperitoneal routes of administration may be employed, generally intravenous is preferred. The skilled artisan will recognize that the route of administration will vary depending on the disorder to be treated.

Determining a therapeutically effective amount of the bi-functional protein, according to this invention, largely will depend on particular patient characteristics, route of administration, and the nature of the disorder being treated. General guidance can be found, for example, in the publications of the International Conference on Harmonisation and in REMINGTON'S PHARMACEUTICAL SCIENCES, chapters 27 and 28, pp. 484-528 (Mack Publishing Company 1990).

Determining a therapeutically effective amount specifically will depend on such factors as toxicity and efficacy of the medicament. Toxicity may be determined using methods well known in the art and found in the foregoing references. Efficacy may be determined utilizing the same guidance in conjunction with the methods described below in the Examples. A pharmaceutically effective amount, therefore, is an amount that is deemed by the clinician to be toxicologically tolerable, yet efficacious. Efficacy, for example, can be measured by the decrease in mass of the targeted tissue. Suitable dosages can be from about 1 mg/kg to 10 mg/kg.

Screening Assays to Determine the Biological Activities of the Fusion Protein

The present invention also provides cell-based assay systems that can be used to compare the biological activities of the receptor antagonizing domain and angiogenesis inhibiting domain, respectively, and/or a fusion protein comprising each of these domains. To this end, antibody binding assays are used to ensure that the fused domains of the fusion protein are being expressed. Competitive binding assays may be used to ensure that each domain of the fusion protein binds to its normal receptor.

By introducing to a cell line various concentrations of a particular domain in its antagonized, non-antagonized, and fused forms, one of skill in the art could determine the biological activity of the apoptosis-promoting domain of the fused protein vis-à-vis the same domain in its non-fused state. There are numerous ways to measure apoptosis. These methods include, but are not limited to the following techniques: (1) Loss of cell viability—measured by a failure to either exclude vital dye or uptake MTT (3-(4,5-dimethylthiazol-2-yl)-2,5-diphenyltetrazolium bromide), or MTS-PMS; (2) DNA fragmentation—assayed by agarose gel electrophoresis, PFG electrophoresis, in situ terminal transferase labeling (TUNEL); Cell and nuclear morphology—employing microscopy to visualize chromatin condensation, DNA organization, and cytoplasmic integrity; and Cysteine protease activation assays—utilizing caspase activation assays combined with calorimetric or fluorescent readouts, poly (ADP-ribose) polymerase (PARP) or laminin cleavage by western blot or immunohistochemistry.

Likewise, a cell line that can measure activity of the angiogenesis inhibiting domain should be similarly used to monitor the activity of this domain of the fusion protein. Examples 7 and 8, which use human umbilical vein endothelial cell proliferation and organization assays, are possible, yet non-limiting methods to determine biological activity of the angiogenesis inhibiting domain in the fusion protein.

The following examples are intended to be illustrative and not limiting.

EXAMPLES

Example 1: Cloning and Construction of Expression Vectors for hPRL-Angiogenesis Inhibitor Expression A two-step cloning procedure based upon published protocols (Catado et al., 2000) was used to generate recombinant DNA encoding hPRL-G129R fused to endostatin, angiostatin or Flk-1-BP, making a G129R-endostatin (G129R-endo), G129R-angiostatin, and G129R-Flk-1-bp fusion protein, respectively. Human endostatin, angiostatin, or Flk-1-bp were PCR amplified from Universal Quick-Clone cDNA (Clontech, Calif.). Each of the amplified cDNA fragments were first be cloned independently into a pCR2.1 TA cloning vector (Invitrogen, Inc.; Carlsbad, Calif.) and their sequences were confirmed.

For instance, Primers corresponding to G129R (5' primer; restriction site for NdeI: 5'-CAT ATG TTG CCC ATC TGT CCC GGC-3' and 3' primer; restriction site for BamHI: 5'-GGA TCC GCA GTT GTT GTT GTG GAT-3') were used to amplify the G129R fragment from a previous clone (Chen et al., Clin. Cancer Res., 5:3583-3593 (1999)). Primers corresponding to human endostatin (5' primer; restriction site for BamHI: 5'-GGA TCC CAC AGC CAC CGC GAC TTC CAG-3' and 3' primer; restriction site XhoI with stop codon: 5'-CTC GAG CTA CTT GGA GGC AGT CAT GAA GC-3') were used to amplify the gene from a Human Universal QUICK-Clone cDNA library (Clontech, Palo Alto, Calif.). Another 5' primer, NdeI: 5'-CAT ATG CAC AGC CAC CGC GAC TTC CAG, was used with the XhoI 3' primer for expression of human endostatin alone. All cDNA fragments were ligated separately into the TA cloning vector pCR2.1 (Invitrogen, Inc., Carlsbad, Calif.), restriction mapped and sequenced.

The cloned cDNA fragments were then re-isolated by restriction digestion, purified and ligated into the pET22b+ expression vector (Novagen, Madison, Wis. All three cDNA were cloned initially as full-length cDNA encoding mature form of proteins for *E. coli* expression using pET22b expression vector. The cDNAs then were amplified by PCR with second set of primers that designed to yield products lacking translational start codon and having a BamHI restriction site at 5' end (before the +1 site, for in frame ligation with G129R cDNA) and an XhoI site after the stop codon. The fragment will then be treated with restriction enzymes (BamHI and XhoI) and ligated with G129R cDNA to create pET22b G129R-fusion plasmids for G129R-endostatin, G129R-Angiostatin, and G129R-Flk-1-BP.

Example 2

Transfecting an Expression Plasmid into a Stable Cell Line

*E. coli*, such as BL21(DE3) cells (Novagen, Madison, Wis.), were transformed with plasmids encoding G129R fusion proteins using the calcium chloride method. Bacteria were allowed to grow overnight in Luria-Bertani (LB) broth (ampicillin 50 µg/ml) at 37 C. The following day a LB growth culture was generated by inoculation of 5% of the seed culture and grown for ≈2.5 hours at 37° C. with agitation.

Example 3

Purifying the Fusion Protein

Figure 6:
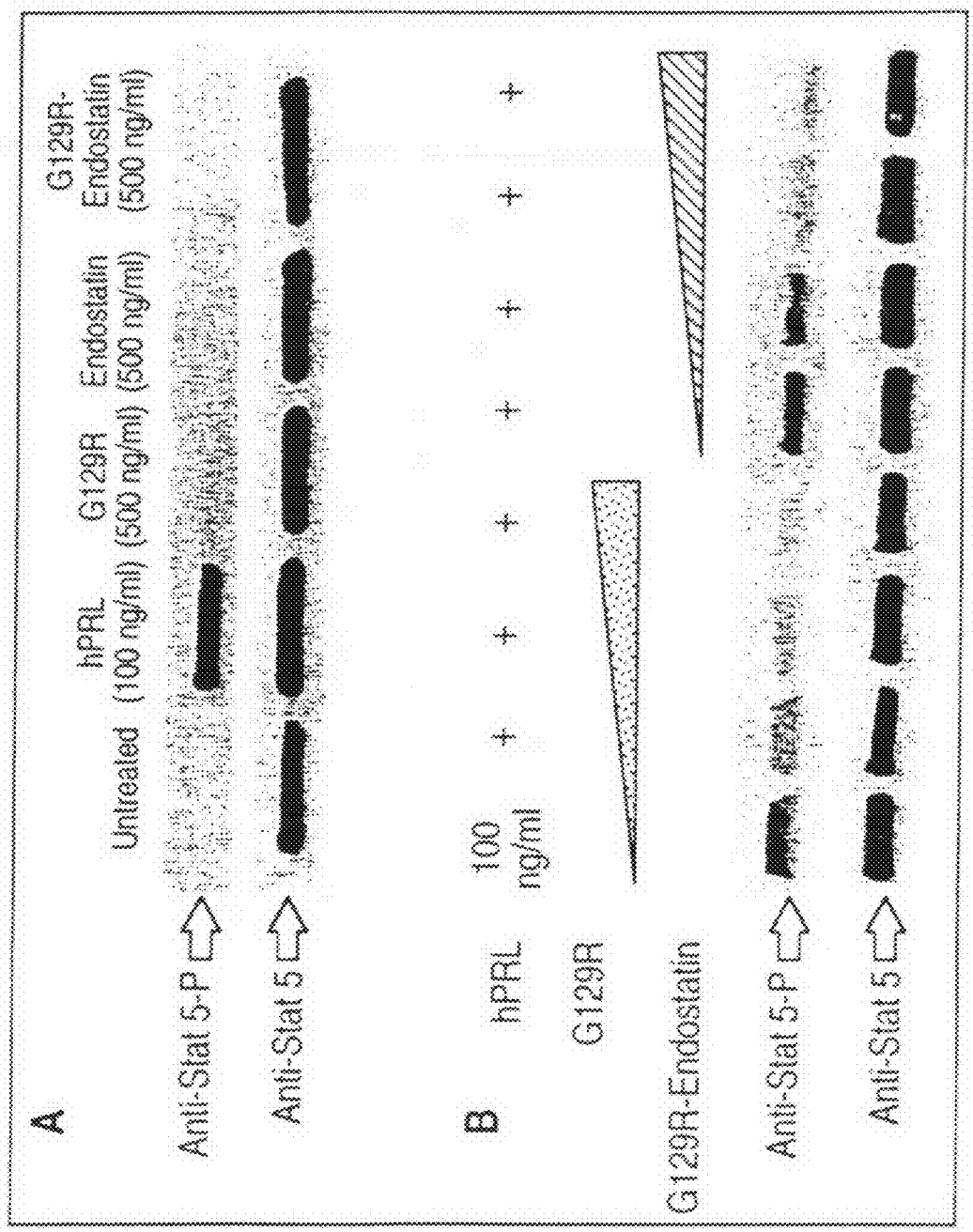
FIG. 6. Inhibition of STAT-5 phosphorylation by G129R-Endostatin. T-47D human breast cancer cells were treated with the indicated amounts of PRL, G129R and G129R-Endostatin (A) or a dose dependent combination treatment (B). Total protein was extracted and analyzed on a 4-15% gradient SDS-PAGE, followed by Western blotting with antiserum against either STAT-5-phosphorylated or STAT-5 as indicated in the appropriate panel. A, Inhibition or stimulation of STAT5 phosphorylation of T-47D cells by PRL, G129R, endostatin and G129R-Endostatin. B, Dose-dependent competitive inhibition of STAT-5-phosphorylation by G129R-Endostatin. T-47D cells were incubated with PRL and increasing concentrations of G129R or G129R-Endostatin. STAT5 and phosphorylated-STAT5 were detected by Western blot analysis as described in the materials and methods.

Cells were transformed and grown as described in Example 2. IPTG (Fisher Scientific) was added to the culture (1 mM final concentration) to induce expression of G129R fusion proteins and incubated for an additional 4 hours. Bacteria were pelleted and resuspended in a solution containing 0.2M $NaPO_4$ pH 8, 10 mM EDTA, and 0.5% Triton X-100. The resuspended bacteria were lysed with a 550 Sonic Dismembrator (Fisher Scientific). The products, which were present in the form of inclusion bodies, were pelleted at 12,000 g for 15 minutes and resuspended in 0.2M $NaPO_4$ pH7, 1% v/v beta mercaptoethanol, and 8M Urea for refolding. The refolding process consists of dialyzing the protein against decreasing amounts of urea and beta-mercaptoethanol in the presence of 50 mM $NH_4HCO_3$ pH 8.0 for three consecutive days. The sample was first filtered through a 0.22 micron filter (VWR), degassed and then purified by Sepharose ionic exchange columns followed by Sephacryl gel filtration columns (Pharmacia, Piscataway, N.J.) using a FPLC system (Pharmacia, Piscataway, N.J.).

The samples of the purified proteins were run on a 12% SDS-PAGE gel and stained with Coumassie Blue. As shown in FIG. 3, the fusion proteins has an apparent molecular weight that is consistent with expression of both domains. Furthermore, as shown in FIG. 4, expression of both domains of the fusion protein was confirmed using Western analysis using specific antibodies (CalBiochem, San Diego, Calif. 92121: human endostatin, cat #324746; Rabbit Anti-human endostatin, cat# PC266; human angiostatin, cat#176700; anti-angiostatin, cat#PC371; R&D Systems, Minneapolis, Minn. 55413: human Flk-1-BP, cat#357-KD-050; anti-human Flk-1-BP polyclonal antibody, cat#AF357). The purity of the fusion proteins was determined by comparing the results of the IRMA and a standard protein assay (Biorad, Hercules, Calif.). G129R fusion proteins produced by this method have an extra Met at the N-terminus as compared to wild type PRL.

All proteins used in this project were purified using two column procedures, i.e. ionic exchange followed by size exclusion columns using a FPLC system. The purified proteins were tested for endotoxin levels through Cape Cop Inc. The endotoxin levels were approximately 5 EU/mg protein, which is considered acceptable for mouse studies.

Example 4

Testing the Biological Activities of Purified hPRL and hPRL-G129R Via Competitive Radioreceptor Binding Assay Radioreceptor binding assays were performed as previously described (Chen et al., 1991; Appendix B). Briefly, T-47D cells will be grown in six-well tissue culture plates until 90% confluent (~$10^5$ cells/well). Monolayers of cells were starved in serum-free RPMI-1640 medium for 2 h. The cells were then incubated at room temperature for two hours in serum-free RPMI-1640 containing $8\times10^4$ cpm $^{125}$I hPRL (Specific Activity=30 μCi/μg; NEN Dupont, Boston, Mass.) with or without hPRL, hPRL-G129R, endostatin, or GEFP at various concentrations. Cells were then washed three times in serum-free RPMI-1640 and solubilized in 0.5 ml of 0.1N NaOH/1% SDS, and the bound radioactivity was determined by a Gamma counter (ICN Biomedical, model 4/600plus; Costa Mesa, Calif.). The resulting data are shown in FIG. 5.

These data show that PRL, G129R and G129R-Endostatin all competitively displaced the $^{125}$I-hPRL from the PRLR on T-47D cells with similar affinity, whereas endostatin did not, suggesting that G129R-Endostatin retained its PRLR recognition ability.

Example 5

Testing the Biological Activities of Purified GEFP Via STAT 5 Phosphorylation/Immunoprecipitation Assay T-47D cells were grown in RPMI-1640 medium containing 10% Charcoal Stripped Fetal Bovine Serum (CSFBS; growth medium). For each experiment, cells were passed into 6 well culture plates in growth medium and cultured to 90% confluency. On the day of the experiment, cells were depleted in serum free media for one hour and incubated in hPRL, G129R or combination of two for 30 min. After treatment, T47-D cells were washed once with ice-cold PBS and collected by gentle scraping in 1 ml ice-cold lysis buffer [20 mM Tris-Cl (pH 7.4), 100 mM NaCl, 2 mM EDTA, 1% NP-40, 1 mM phenylmethylsulfonyl fluoride, 10 ug/ml aprotinin, 10 ug/ml leupeptin]. The lysis mixture was then passed through a 22 gauge needle several times avoiding air bubbles and centrifuged at 12,000×g for 20 minutes. The supernatant was then transferred to a new microcentrifuge tuber. Five μg of STAT5 monoclonal antibody will then be added to 100 microliters (200-500 micrograms total protein) of cell lysate along with 400 microliters of $ddH_2O$ and 500 microliters of 2×IP buffer [1% Triton X-100, 150 mM NaCl, 10 mM Tris pH 7.4, 1 mM EDTA, 1 mM EGTA, 0.2 mM sodium vanadate, 0.2 mM PMSF, 0.5% NP-40] to each reaction. After overnight incubation at 4° C. and gentle rotation, 50 microliters of prewashed (1×IP buffer) protein A agarose beads were added to each IP reaction and continue the Incubation for another 2 hours at 4° C. The agarose beads were washed 3× with 1×IP buffer and the protein will then be eluted by resuspending the protein A agarose beads in 50 microliters of 1×SDS PAGE loading buffer. Samples were then be subjected to 4-12.5% SDS-PAGE and immune blot analysis using horse radish peroxidase (HRP) conjugated anti-phosphotyrosine antibody PY20 and ECL reagent kit (Amersham, Ill.). As shown in FIG. 6, blots were exposed to X-ray films and developed using standard procedures (Kodak, Rochester, N.Y.).

STAT5 phosphorylation is one indicator of PRL-mediated signal transduction in mammary cells, and we have used STAT5 phosphorylation assay as a measure of the antagonistic effects of G129R and its variants (Cataldo et al., Int. J. Oncol., 17:1179-1185 (2000)). The status of STAT5 phosphorylation was examined by treating T-47D cells with PRL, G129R, endostatin and G129R-Endostatin. As shown in FIG. 6A, PRL (100 ng/mlm) induces STAT5 phosphorylation, whereas G129R, endostatin and G129R-Endostatin lack the ability to induce STAT5 phosphorylation. A dose dependent competitive inhibition of PRL induced STAT5 phosphorylation was observed for G129R and G129R-Endostatin (FIG. 6B). G129R and G129R-Endostatin exhibited similar potency in the inhibition of STAT5 phosphorylation. This demonstrates that the G129R portion of G129R-Endostatin retained its antagonistic effects to PRLR.

Example 6

Immunofluorescence Staining

T-47D and HUVEC cells were maintained as previously described. Cells were passed onto Lab-Tek Chamber Slide System (Fisher Scientific) and grown to approximately 70% confluency. HUVEC cells were cultured in low serum medium (2% FBS) and T-47D cells were serum depleted for 30 min. Cells were treated with either 10 µg/ml of G129R, 10 µg/ml of endostatin or 20 µg/ml of G129R-Endostatin for 30 min at 37° C. Cells were treated in their respected serum-free media, and all staining was performed in triplicate and repeated at least twice. After treatment, cells were washed with phosphate buffered saline (PBS) [NaCl 120 mmol; KCl 2.7 mmol; phosphate buffer salts 10 mmol; pH=7.4], fixed with 4% Para-Formaldehyde (BD Biosciences, Bedford, Mass.) for 25 min at 4° C. and permeabilized with 0.2% Triton-X-100 in 1×PBS. Cells were incubated in blocking buffer for 30 min with 2% Bovine Serum Albumin (BSA; Fisher Scientific). Cells were incubated with the primary antibodies rabbit anti-human Endostatin (Ab-2), 1:200, and mouse anti-human PRL antiserum, 1:1000, at room temperature for 2 h. After incubation, cells were washed three times with 1% BSA/PBS and subjected to secondary antibody (1:500) incubation for 2 h at room temperature using Alexa Fluor 594 goat anti-mouse IgG (red fluorescence) and Alexa Fluor 488 goat anti-rabbit IgG (green fluorescence) (Molecular Probes, Inc., Eugene, Oreg.), respectively. Cells were rinsed twice with 1% BSA/PBS and incubated with Anti-Fade equilibrium buffer (10 µl/well) (Molecular Probes) for 10 min at room temperature. The chambers were then removed and cover slides were mounted for observation. All wells were examined under an Olympus IX70 fluorescent microscope using 488 nm and 594 nm wavelengths. Digital photographs were taken at 450× magnification.

An immunofluorescence assay was used to determine if G129R-Endostatin has the ability to bind to both breast cancer and endothelial cells (FIG. 12). HUVEC and T-47D cells were treated with G129R, endostatin or G129R-Endostatin and stained with protein specific primary antibodies. Fluorescent secondary antibodies were used to distinguish G129R (Alexa Flour 594, Red) and endostatin (Alexa Flour 488, Green). FIG. 12, Panels A and B represent the untreated HUVEC and T-47D cells as controls. As shown in FIG. 12 Panels C and D, G129R-Endostatin binds to HUVEC and T-47D cells respectively. This is demonstrated by the fluorescence of both the endostatin antibody (green) and the PRL antibody (red) in the same field of view. Endostatin binds to HUVEC's (FIG. 12 Panel E) and binds to what appears to be the extracellular matrix of T-47D cells with a scattered staining pattern (FIG. 12 Panel F). In contrast, G129R binds only to T-47D cells (Panel H), but it does not bind to HUVEC's (FIG. 12 Panel G). It is interesting to point out that there is a distinct pattern of staining between G129R and endostatin. G129R and G129R-Endostatin treatments revealed a clear cellular staining pattern in T-47D cells (FIG. 12 Panels D and H). Whereas, endostatin-treated cells demonstrate a scattered staining pattern in both HUVEC and T-47D cells (FIG. 12 Panels C, E, and F). It is clear that G129R does not bind to HUVEC's due to the lack of PRLR on these cells (Panel G). The staining in Panel C is most likely due to the endostatin portion of the fusion protein binding to the HUVEC's.

Example 7

Testing the Angiogenesis Inhibitory Effect of GEFP Using a Human Umbilical Vein Epithelial Cell (HUVEC) Proliferation Assay HUVEC's and T-47D cells were grown in their respective phenol-red free medium. Fully confluent HUVEC and T-47D cell cultures were trypsinized and cells were resuspended in medium containing 5% FBS. Cells were then seeded into 96-well culture plates at a density of 5,000 HUVEC's/well (in the presence of 2.5 ng/ml of basic fibroblast growth factor (bFGF) (Sigma) in the presence of 1 µg/ml of heparin (Sigma)) and 15,000 T-47D cells/well. After an incubation of 24 h, various concentrations of G129R, endostatin, or G129R-Endostatin were added to the appropriate well. Cells were further incubated for 72 h at 37° C. in a humidified 5% $CO_2$ incubator. The viability of the cells was determined using the MTS-PMS (CellTiter 96 Aqueous Kit; Promega Corp., Madison, Wis.) colorimetric assay (following the manufacturer's instructions), and absorbance at 490 nm was determined using a microplate reader (Bio-Rad). Cell survival was calculated as a percentage of the control values. All experiments were carried out in triplicate.

Cell proliferation assays were carried out to examine the dual effects of G129R-Endostatin in inhibiting the proliferation of both HUVEC and T-47D cells. G129R-Endostatin revealed to be as effective as endostatin in inhibiting the proliferation of HUVEC cells in a dose dependent manner (FIG. 13A). The $EC_{50}$ of G129R-Endostatin is similar to that of endostatin at approximately 500 ng/ml (FIG. 13A). G129R had no effect on HUVEC cell proliferation, suggesting that the inhibitory effect of G129R-Endostatin was due to the endostatin domain in the fusion protein. On the other hand, G129R-Endostatin has anti-proliferative effects on T-47D human breast cancer cells similar to that of G129R, with an $EC_{50}$ of ~750 ng/ml (FIG. 13B). As expected, endostatin had no effect on the proliferation of T-47D cells.

Figure 7A:
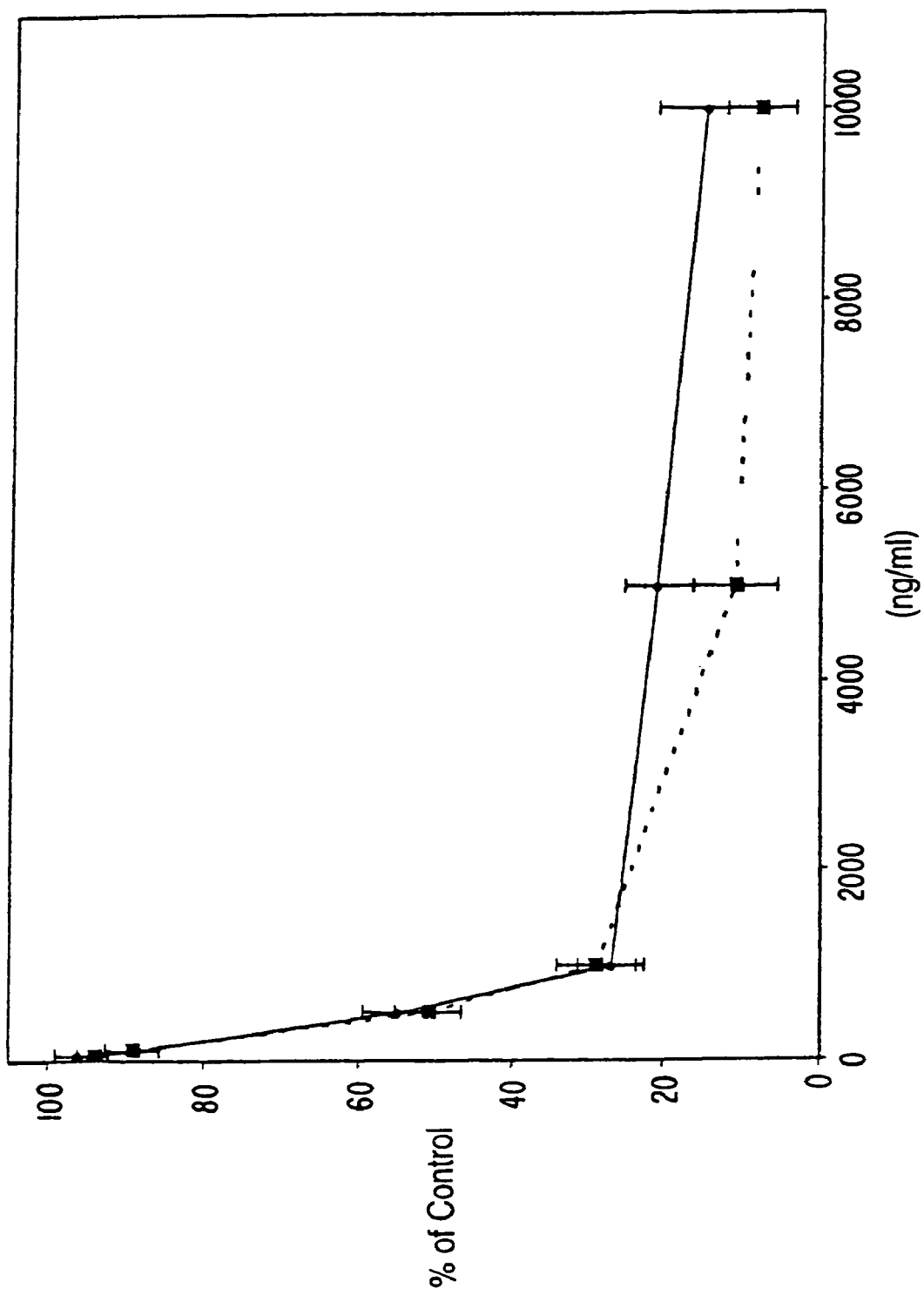
FIG. 7. Endothelial cell proliferation assay. Purified human endostatin and GEFP were tested for their antiproliferative ability using HUVECs (A), T-47D cells (B) and mouse L-cells (C). The solid line represents endostatin and the dashed line represents GEFP treatment. Viability of cells was determined by MTT assay. Values are represented by the percent of viable cells after treatment with either endostatin or GEFP compared to untreated proliferating cells. A, is the ability of endostatin and GEFP to inhibit bFGF-induced endothelial cell proliferation. B, represents the effects of endostatin and GEFP to inhibit the proliferation of human breast cancer cell line T-47D. C, represents a non-endothelial cell proliferation assay as the negative control in this experiment. Each experiment was carried out in triplicate and the values are represented as the means±SD.
Figure 7B:
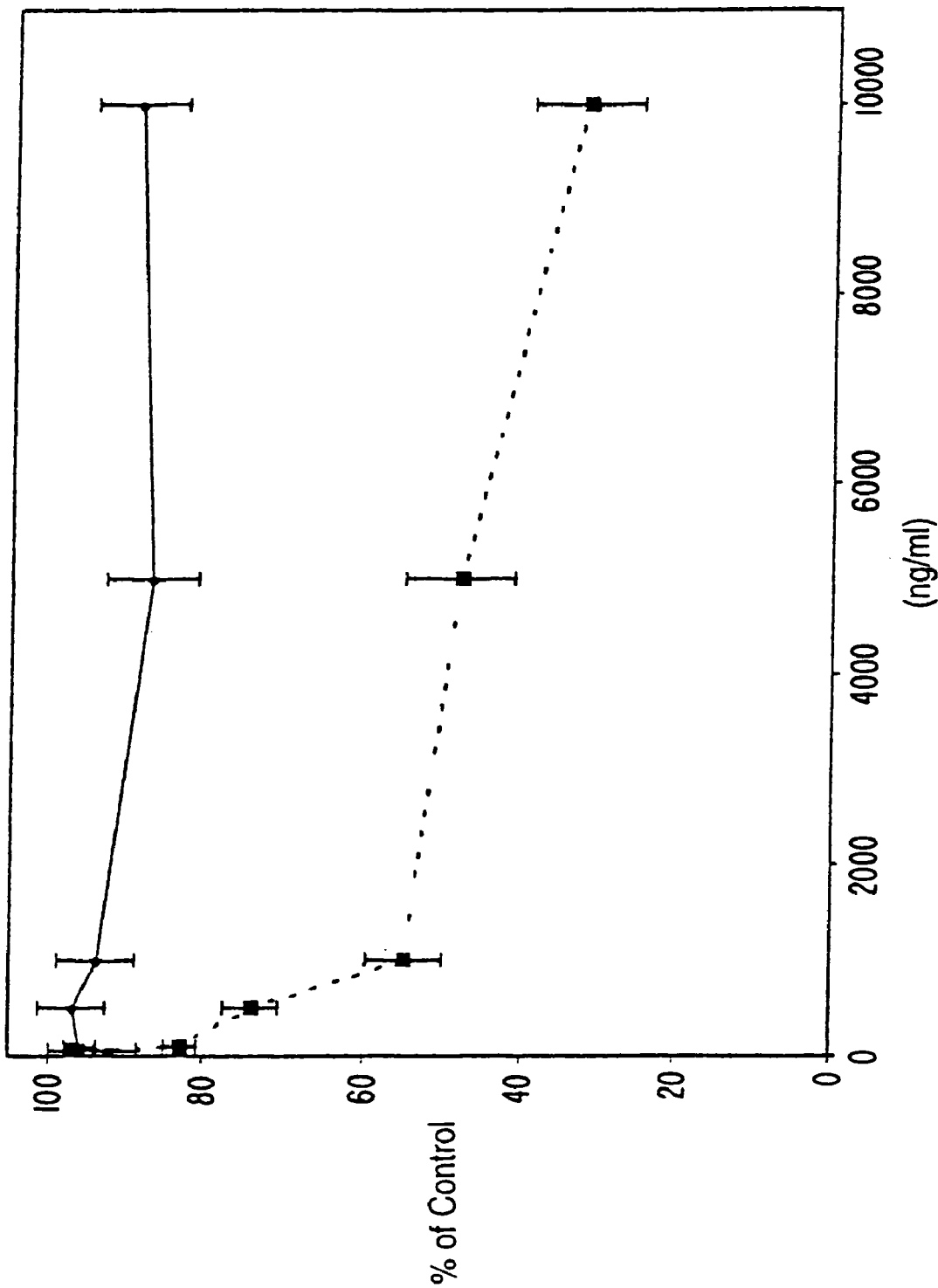

In another experiment, the cell proliferation assay for HUVEC cells followed the procedure described by Bae et al. Briefly, HUVEC cells were seeded in gelatin-coated 48-well plates at a density of $1 \times 10^5$ cells/well in 300 µL of growth media and were incubated for 2 days at 37° C. Plates were washed 3× with warm, serum-free growth medium before 200

µL of serum-free growth medium was added to the negative control and normal growth media was used for the positive control, as well as for the experimental samples. In the experimental samples, 500 ng/mL of protein was tested. These plates were allowed to incubate a day at 37° C. Next, 0.5 µCi of methyl-[$^3$H]thymidine in 20 uL was added to each well and allowed to incubate a day at 37° C. The plates were then washed 4× with PBS containing 0.1% BSA, and the cells were solubilized with 150 µL 0.4N NaOH at room temperature for 20 min. To neutralize this reaction, 30 µL of 2N HCl was added to each well, and the contents were transferred to scintillation vials to determine the radioactivity of each sample in a scintillation counter. This experiment was carried out in triplicate and the resulting data is shown in FIG. 7.

Example 8

Determination of GEFP Ability to Inhibit HUVEC Organization

This assay generally followed a known procedure. (Morales et al. 1995) HUVECs were maintained in Leibovitz's medium containing 10% FBS. Prior to culture, 24-well culture plates were prepared by coating wells with Matrigel (polymerization for 30 min at 37° C.). HUVEC (1×10$^5$) suspended in 1 ml of Leibovitz medium, with or without the GEFP along with controls, was added into each well. Cells were incubated at 37° C. overnight. After removal of the culture medium, the culture was fixed with Diff Quick (Dade Behring Inc. Newark, Del.). The area of the endothelial tube network in each culture was examined microscopically by the Optomax-Olympus microscope (FIG. 8).

Prominent tubal structures were demonstrated by the control cells (FIG. 8). At low concentrations (100 ng/ml) both endostatin and G129R-Endostatin begin to disrupt the formation of the tubes, indicated by the arrows. At high concentrations (1,000 ng/ml) both endostatin and G129R-Endostatin treatments eliminated the tubal structures, and the cells appear to be dying. G129R treatment, serving as a negative control, had no obvious effects on endothelial tube formation.

Example 9

Inhibition of Human Breast Cancer in Mice

Eight athymic nude mice were inoculated subcutaneously with 1×10$^6$ T-47D cells mixed with Matrigel. Tumors were allowed to grow for 21 days. Mice were randomized and divided into two equal groups. One group was injected with GEFP (10 mg/kg/mouse); the other group was injected with 100 µl of sterile saline (speckled) for 25 consecutive days. Tumor volume, calculated on day 12 and day 25 post treatment using the equation: [(short dimension$^2$)×(long dimension)]/2, is shown in FIG. 9.

Example 10

Pharmacokinetic Methods

Female Balb/c mice (Jackson Lab, Bar Harbor, Me.) were used to determine the serum half-life of G129R-Endostatin. Two hundred micrograms of G129R or 200 µg of G129R-Endostatin was injected (i.p.) into Balb/c mice (n=4). Blood samples were obtained from each mouse at time intervals of 2, 4, 8, and 24 h by tail vein bleeding. Samples were placed on ice and immediately centrifuged for 5 min at 4° C. The serum was collected and frozen at −20° C. until further use. The serum concentration of both G129R and G129R-Endostatin was determined using the hPRL IRMA kit (DPC, Inc.). Area under the curve (AUC) was calculated by linear trapezoidal method from 0 to 24 h.

It has been demonstrated that increasing the size of a protein may increase its half-life (Zhang et al., *Clin. Cancer Res.*, 8:1196-1205 (2002)). The relative short serum half-life of G129R and endostatin present a considerable challenge to the clinical use of these potential therapeutic agents. To examine whether the pharmacokinetics, namely half-life, of G129R-Endostatin are increased compared to G129R alone the relative serum half-life was assessed. As shown in FIG. 14, the half-life of G129R-Endostatin was extended to more than triple that of G129R. Four hours after a single injection (i.p.), G129R was no longer detected in serum, whereas G129R-Endostatin levels remained at approximately 1,500 ng/ml, and remained detectable in serum for approximately 24 hours. The calculated AUC of G129R-Endostatin was found to be approximately 3.21 fold higher than that of G129R (FIG. 14).

Example 11

In Vivo Studies of hPRL-G129R-Endo Fusion Protein

Two breast cancer cell lines, T-47D and 4T1, were used to investigate the anti-tumorigenic effects of a hPRL-G129R-Endo fusion protein. 8 control animals were treated with G129R-endostatin fusion protein after nude mice were innoculated with T47D tumor cells (n=4) or 4T1 tumor cells (n=4). The results are depicted in FIGS. 10A and 10B, respectively.

Figure 10A:
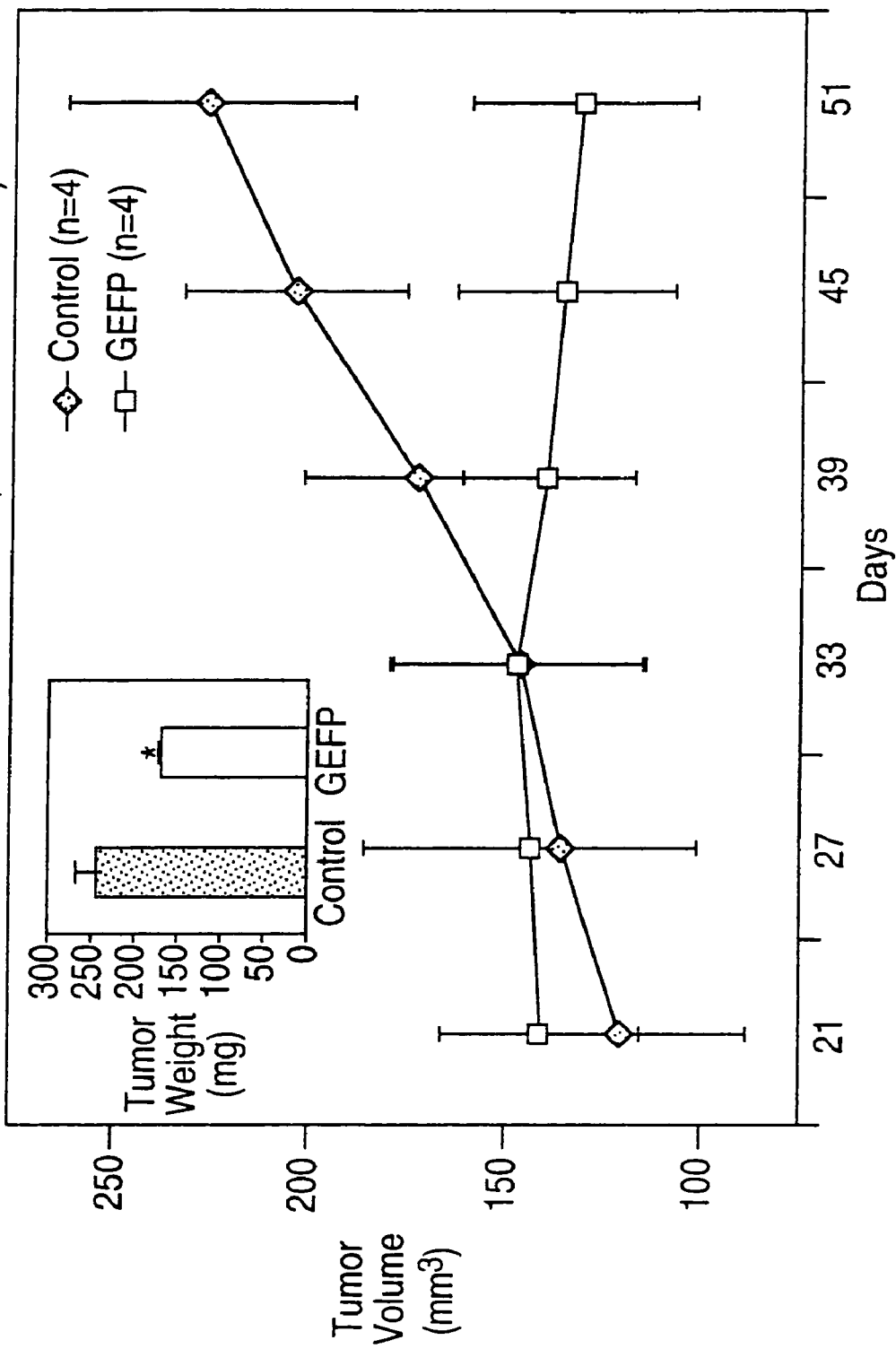
Figure 10B:
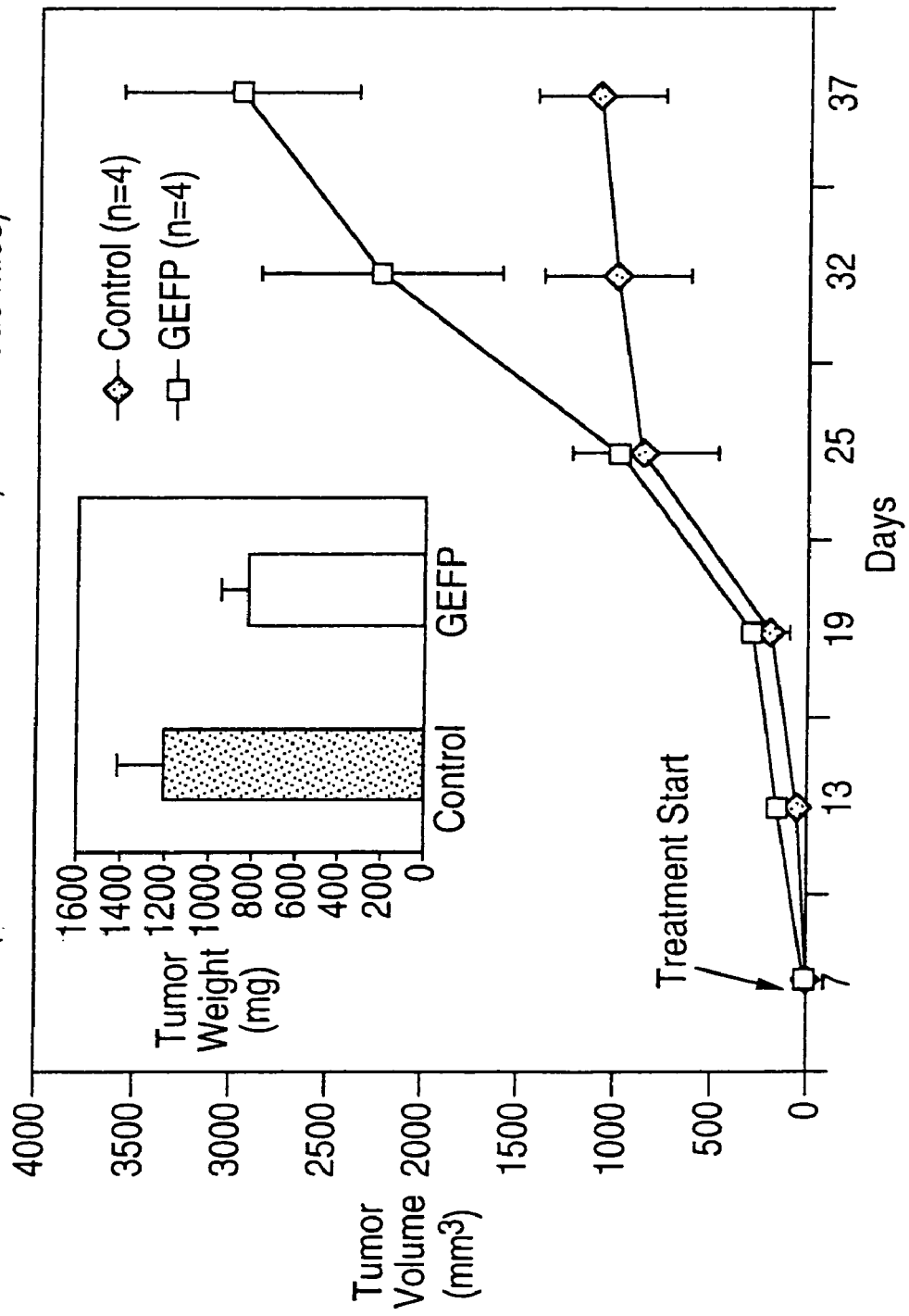

FIG. 10A demonstrates the ability of GEFP to inhibit T-47D induced tumor growth in nude mice. The tumor was allowed to establish itself for 3 weeks before any treatment was performed and tumor volume was calculated every six days. Control animals (n=4) were injected with 100 ul of PBS and GEFP treated mice (n=4) were treated (via i.p. injection) with 200 ug total protein in 100 ul volume. The tumor growth rate slowed in GEFP treated animals. At the conclusion of the experiment, tumors were removed and weighed. The insert in FIG. 10A represents the tumor weight from the control and GEFP treated mice.

The therapeutic efficacy of GEFP was confirmed using a mouse breast cancer cell line 4T1 in vivo. FIG. 10B demonstrates that GEFP is effective in inhibiting tumor growth in an animal model of aggressive mouse breast cancer (4T1). This cell line established itself for one week prior to GEFP treatment. GEFP treatment started everyday for 37 days (200 ug/daily, i.p.). The significant difference in tumor growth rate between the control mice and the treated mice can be appreciated. G129R-Endostatin has a serum half-life more than 3-fold that of G129R alone, and exhibited greater tumor inhibitory effects than G129R, endostatin individually or in combination. Taken together, these data demonstrate the dual therapeutic effects of G129R-Endostatin, and suggests that G129R-Endostatin has great promise as a novel anti-breast cancer agent. The insert in FIG. 10B represents the tumor weight from the control and GEFP treated mice.

In vivo studies were further considered and results are provided in FIG. 15. The in vivo anti-tumor efficacy of G129R-Endostatin was examined using a 4T1 mouse mammary xenograft in an athymic nude mouse model. Female athymic nude (nu/nu) mice (Jackson Lab) 6-8 weeks of age were randomly placed into groups of 5 mice per cage, 2 cages per treatment for a total of ten mice per group. Each mouse was injected with 4T1 breast cancer cells (5×10⁴) and tumors were allowed to establish for 5 days. Once tumors were established, mice were subjected to daily i.p. injections of different agents as designed. Treatment groups including G129R (2.5 mg/kg/day), endostatin (2.5 mg/kg/day), G129R-Endostatin (5 mg/kg/day), and a combination of G129R (2.5 mg/kg/day) and endostatin (2.5 mg/kg/day) and control group were administered in a volume of 100 μl. Control groups were given 100 μl/injection of sterile PBS. Measurements of tumors were recorded every five days until it was decided that tumors were debilitating to the mice. The long axis (L) and the short axis (S) were measured and the tumor volume was calculated using the following equation: $[(S)^2 \times L]/2$. Once final measurements were taken the mice were sacrificed by cervical dislocation, tumors were dissected, weighed, and flash frozen in liquid nitrogen for future analysis.

Figure 15A:
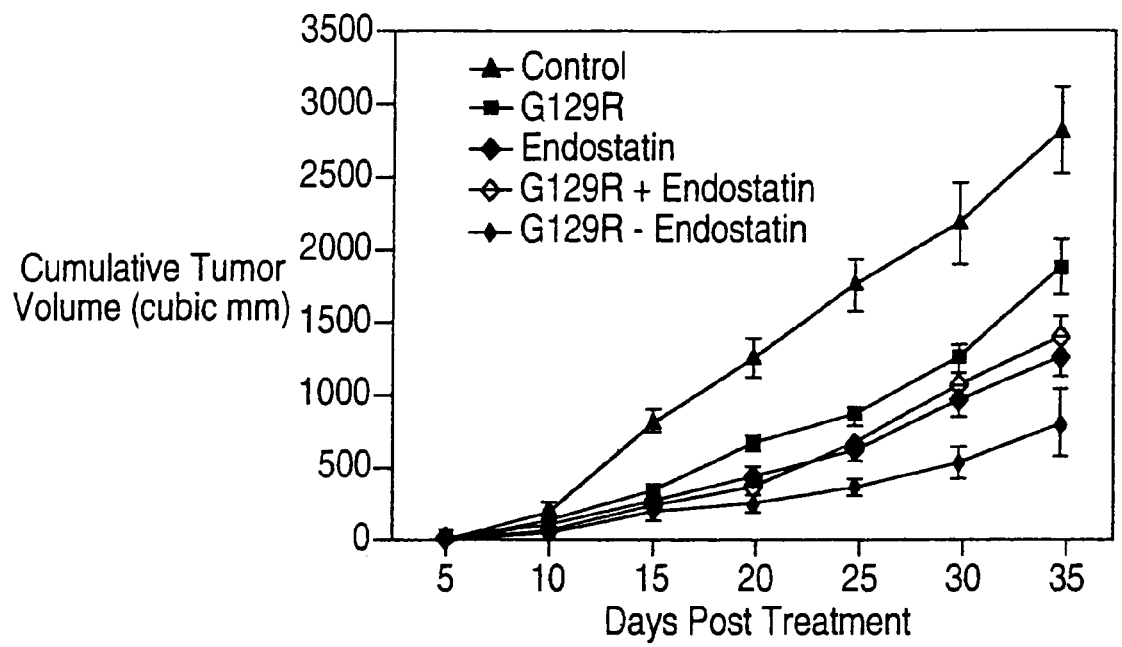
Figure 15B:
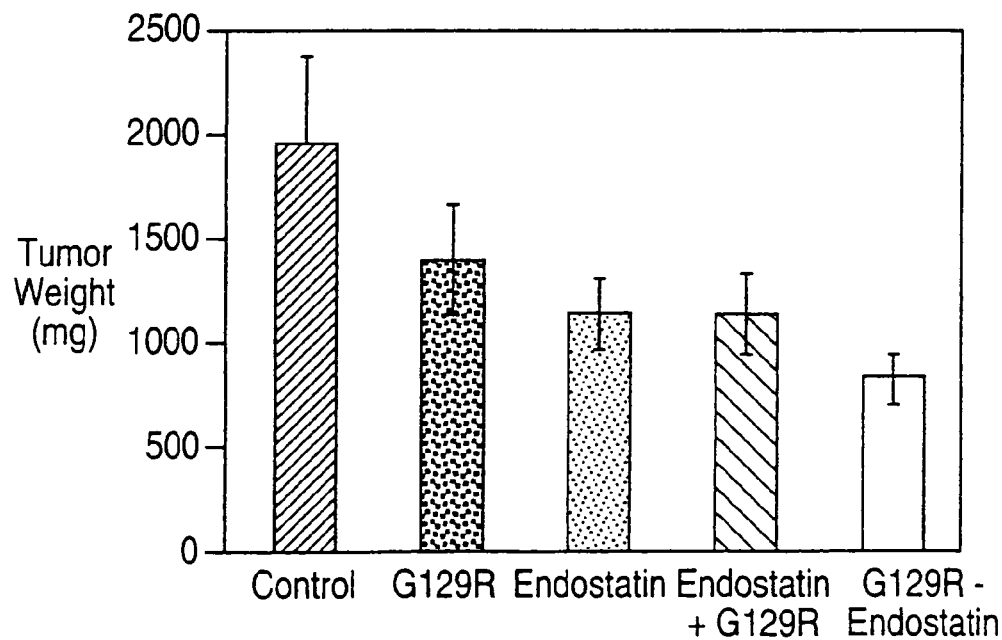

Among the four treatment groups, G129R-Endostatin (807±235 mm³) demonstrated the best inhibitory effects on 4T1 tumor growth compared to control group (2,851±305 mm³), G129R (1,897±194 mm³), endostatin (1,271±142 mm³), and the combination treatment (1,399±147 mm³) (FIG. 15A). The final tumor weights at the end of the experiment were: G129R-Endostatin (841±121 mg); control (1,970±410 mg), G129R (1,409±265 mg), endostatin (1,159±170 mg), and the combination of G129R and endostatin (1,149±195 mg) (FIG. 15B).

These examples are provided for illustrative purposes are not intended to limit the scope of the invention in any manner. It will be recognized by one of skill in the art that fusion proteins within the scope of the present invention may be created by a variety of means without departing from the spirit or scope of the present invention.

What is claimed is:

1. A method for treating breast or prostate cancer expressing a prolactin receptor, comprising administering to a patient an effective amount of a protein having a receptor-antagonizing domain and an angiogenesis-inhibiting domain, wherein the angiogenesis-inhibiting domain is endostatin and wherein the receptor-antagonizing domain is a prolactin-antagonist domain characterized by a single amino acid substitution at the position corresponding to 129 of the human prolactin protein, wherein said amino acid substitution is a glycine to an arginine.

2. A method according to claim 1, wherein the protein is a prolactin antagonist-endostatin fusion protein.

3. A method according to claim 2, wherein the prolactin-antagonist domain comprises a protein having the amino acid sequence of SEQ ID NO.: 1 (hPRLA).

* * * * *

SEQUENCE LISTING

<160> NUMBER OF SEQ ID NOS: 45

<210> SEQ ID NO 1
<211> LENGTH: 200
<212> TYPE: PRT
<213> ORGANISM: Homo sapiens

<400> SEQUENCE: 1

Met Leu Pro Ile Cys Pro Gly Gly Ala Ala Arg Cys Gln Val Thr Leu
 1               5                  10                  15

Arg Asp Leu Phe Asp Arg Ala Val Val Leu Ser His Tyr Ile His Asn
            20                  25                  30

Leu Ser Ser Glu Met Phe Ser Glu Phe Asp Lys Arg Tyr Thr His Gly
        35                  40                  45

Arg Gly Phe Ile Thr Lys Ala Ile Asn Ser Cys His Thr Ser Ser Leu
    50                  55                  60

Ala Thr Pro Glu Asp Lys Glu Gln Ala Gln Gln Met Asn Gln Lys Asp
65                  70                  75                  80

Phe Leu Ser Leu Ile Val Ser Ile Leu Arg Ser Trp Asn Glu Pro Leu
                85                  90                  95

Tyr His Leu Val Thr Glu Val Arg Gly Met Gln Glu Ala Pro Glu Ala
            100                 105                 110

Ile Leu Ser Lys Ala Val Glu Ile Glu Glu Gln Thr Lys Arg Leu Leu
        115                 120                 125

Glu Arg Met Glu Leu Ile Val Ser Gln Val His Pro Glu Thr Lys Glu
    130                 135                 140

Asn Glu Ile Tyr Pro Val Trp Ser Gly Leu Pro Ser Leu Gln Met Ala
145                 150                 155                 160

Asp Glu Glu Ser Arg Leu Ser Ala Tyr Tyr Asn Leu Leu His Cys Leu
                165                 170                 175

Arg Arg Asp Ser His Lys Ile Asp Asn Tyr Leu Lys Leu Leu Lys Cys
            180                 185                 190

Arg Ile Ile His Asn Asn Asn Cys
        195                 200

<210> SEQ ID NO 2
<211> LENGTH: 603
<212> TYPE: DNA
<213> ORGANISM: Homo sapiens

<400> SEQUENCE: 2

```
atgttgccca tctgtcccgg cggggctgcc cgatgccagg tgacccttcg agacctgttt      60
gaccgcgccg tcgtcctgtc ccactacatc cataacctct cctcagaaat gttcagcgaa     120
ttcgataaac ggtatacccc tggccggggg ttcattacca aggccatcaa cagctgccac     180
acttcttccc ttgccacccc cgaagacaag gagcaagccc aacagatgaa tcaaaaagac     240
tttctgagcc tgatagtcag catattgcga tcctggaatg agcctctgta tcatctggtc     300
acggaagtac gtggtatgca agaagccccg gaggctatcc tatccaaagc tgtagagatt     360
gaggagcaaa ccaaacggct tctagagcgc atggagctga tagtcagcca ggttcatcct     420
gaaaccaaag aaaatgagat ctaccctgtc tggtcgggac ttccatccct gcagatggct     480
gatgaagagt ctcgcctttc tgcttattat aacctgctcc actgcctacg cagggattca     540
cataaaatcg acaattatct caagctcctg aagtgccgaa tcatccacaa caacaactgc     600
tag                                                                    603

<210> SEQ ID NO 3
<211> LENGTH: 555
<212> TYPE: DNA
<213> ORGANISM: Homo sapiens

<400> SEQUENCE: 3
atgcacagcc accgcgactt ccagccggtg ctccacctgg ttgcgctcaa cagcccctg       60
tcaggcggca tgcggggcat ccgcggggcc gacttccagt gcttccagca ggcgcgggcc    120
gtggggctgg cgggcacctt ccgcgccttc ctgtcctcgc gcctgcagga cctgtacagc    180
atcgtgcgcc gtgccgaccg cgcagccgtg cccatcgtca acctcaagga cgagctgctg    240
tttcccagct gggaggctct gttctcaggc tctgagggtc cgctgaagcc cggggcacgc    300
atcttctcct ttgacggcaa ggacgtcctg aggcacccca cctggcccca gaagagcgtg    360
tggcatggct cggaccccaa cgggcgcagg ctgaccgaga gctactgtga cgtggcgg      420
acggaggctc cctcggccac gggccaggcc tcctcgctgc tggggggcag gctcctgggg    480
cagagtgccg cgagctgcca tcacgcctac atcgtgctct gcattgagaa cagcttcatg    540
actgcctcca agtag                                                    555

<210> SEQ ID NO 4
<211> LENGTH: 184
<212> TYPE: PRT
<213> ORGANISM: Homo sapiens

<400> SEQUENCE: 4

Met His Ser His Arg Asp Phe Gln Pro Val Leu His Leu Val Ala Leu
 1               5                  10                  15

Asn Ser Pro Leu Ser Gly Gly Met Arg Gly Ile Arg Gly Ala Asp Phe
                20                  25                  30

Gln Cys Phe Gln Gln Ala Arg Ala Val Gly Leu Ala Gly Thr Phe Arg
            35                  40                  45

Ala Phe Leu Ser Ser Arg Leu Gln Asp Leu Tyr Ser Ile Val Arg Arg
        50                  55                  60

Ala Asp Arg Ala Ala Val Pro Ile Val Asn Leu Lys Asp Glu Leu Leu
    65                  70                  75                  80

Phe Pro Ser Trp Glu Ala Leu Phe Ser Gly Ser Glu Gly Pro Leu Lys
                85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
```

```
            115                 120                 125
Arg Arg Leu Thr Glu Ser Tyr Cys Glu Thr Trp Arg Thr Glu Ala Pro
        130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180

<210> SEQ ID NO 5
<211> LENGTH: 1158
<212> TYPE: DNA
<213> ORGANISM: Artificial Sequence
<220> FEATURE:
<223> OTHER INFORMATION: Description of Artificial Sequence:
      hPRL_G129R-Endostatin Fusion nucleotide sequence

<400> SEQUENCE: 5
atgttgccca tctgtcccgg cggggctgcc cgatgccagg tgacccttcg agacctgttt      60
gaccgcgccg tcgtcctgtc ccactacatc cataacctct cctcagaaat gttcagcgaa    120
ttcgataaac ggtataccca tggccggggg ttcattacca aggccatcaa cagctgccac    180
acttcttccc ttgccacccc cgaagacaag gagcaagccc aacagatgaa tcaaaaagac    240
tttctgagcc tgatagtcag catattgcga tcctggaatg agcctctgta tcatctggtc    300
acggaagtac gtggtatgca agaagccccg gaggctatcc tatccaaagc tgtagagatt    360
gaggagcaaa ccaaacggct tctagagcgc atggagctga tagtcagcca ggttcatcct    420
gaaaccaaag aaaatgagat ctaccctgtc tggtcgggac ttccatccct gcagatggct    480
gatgaagagt ctcgcctttc tgcttattat aacctgctcc actgcctacg cagggattca    540
cataaaatcg acaattatct caagctcctg aagtgccgaa tcatccacaa caacaactgc    600
ggatcccaca gccaccgcga cttccagccg gtgctccacc tggttgcgct caacagcccc    660
ctgtcaggcg gcatgcgggg catccgcggg gccgacttcc agtgcttcca gcaggcgcgg    720
gccgtggggc tggcgggcac cttccgcgcc ttcctgtcct cgcgcctgca ggacctgtac    780
agcatcgtgc gccgtgccga ccgcgcagcc gtgcccatcg tcaacctcaa ggacgagctg    840
ctgtttccca gctgggaggc tctgttctca ggctctgagg tccgctgaa gcccggggca    900 cgcatcttct cctttgacgg caaggacgtc tgaggcacc ccacctgcc ccagaagagc    960 gtgtggcatg gctcggaccc caacgggcgc aggctgaccg agagctactg tgagacgtgg   1020
cggacggagg ctccctcggc cacgggccag gcctcctcgc tgctgggggg caggctcctg   1080
gggcagagtg ccgcgagctg ccatcacgcc tacatcgtgc tctgcattga gaacagcttc   1140
atgactgcct ccaagtag                                                 1158

<210> SEQ ID NO 6
<211> LENGTH: 385
<212> TYPE: PRT
<213> ORGANISM: Artificial Sequence
<220> FEATURE:
<223> OTHER INFORMATION: Description of Artificial Sequence: Fusion
      protein

<400> SEQUENCE: 6

Met Leu Pro Ile Cys Pro Gly Gly Ala Ala Arg Cys Gln Val Thr Leu
 1               5                  10                  15

Arg Asp Leu Phe Asp Arg Ala Val Val Leu Ser His Tyr Ile His Asn
```

```
                    20                  25                  30
Leu Ser Ser Glu Met Phe Ser Glu Phe Asp Lys Arg Tyr Thr His Gly
            35                  40                  45

Arg Gly Phe Ile Thr Lys Ala Ile Asn Ser Cys His Thr Ser Ser Leu
        50                  55                  60

Ala Thr Pro Glu Asp Lys Glu Gln Ala Gln Gln Met Asn Gln Lys Asp
65                  70                  75                  80

Phe Leu Ser Leu Ile Val Ser Ile Leu Arg Ser Trp Asn Glu Pro Leu
                85                  90                  95

Tyr His Leu Val Thr Glu Val Arg Gly Met Gln Glu Ala Pro Glu Ala
            100                 105                 110

Ile Leu Ser Lys Ala Val Glu Ile Glu Glu Gln Thr Lys Arg Leu Leu
        115                 120                 125

Glu Arg Met Glu Leu Ile Val Ser Gln Val His Pro Glu Thr Lys Glu
    130                 135                 140

Asn Glu Ile Tyr Pro Val Trp Ser Gly Leu Pro Ser Leu Gln Met Ala
145                 150                 155                 160

Asp Glu Glu Ser Arg Leu Ser Ala Tyr Tyr Asn Leu Leu His Cys Leu
                165                 170                 175

Arg Arg Asp Ser His Lys Ile Asp Asn Tyr Leu Lys Leu Leu Lys Cys
            180                 185                 190

Arg Ile Ile His Asn Asn Cys Gly Ser His Ser His Arg Asp Phe
        195                 200                 205

Gln Pro Val Leu His Leu Val Ala Leu Asn Ser Pro Leu Ser Gly Gly
    210                 215                 220

Met Arg Gly Ile Arg Gly Ala Asp Phe Gln Cys Phe Gln Gln Ala Arg
225                 230                 235                 240

Ala Val Gly Leu Ala Gly Thr Phe Arg Ala Phe Leu Ser Ser Arg Leu
                245                 250                 255

Gln Asp Leu Tyr Ser Ile Val Arg Arg Ala Asp Arg Ala Ala Val Pro
            260                 265                 270

Ile Val Asn Leu Lys Asp Glu Leu Leu Phe Pro Ser Trp Glu Ala Leu
        275                 280                 285

Phe Ser Gly Ser Glu Gly Pro Leu Lys Pro Gly Ala Arg Ile Phe Ser
    290                 295                 300

Phe Asp Gly Lys Asp Val Leu Arg His Pro Thr Trp Pro Gln Lys Ser
305                 310                 315                 320

Val Trp His Gly Ser Asp Pro Asn Gly Arg Arg Leu Thr Glu Ser Tyr
                325                 330                 335

Cys Glu Thr Trp Arg Thr Glu Ala Pro Ser Ala Thr Gly Gln Ala Ser
            340                 345                 350

Ser Leu Leu Gly Gly Arg Leu Leu Gly Gln Ser Ala Ala Ser Cys His
        355                 360                 365

His Ala Tyr Ile Val Leu Cys Ile Glu Asn Ser Phe Met Thr Ala Ser
    370                 375                 380

Lys
385

<210> SEQ ID NO 7
<211> LENGTH: 579
<212> TYPE: PRT
<213> ORGANISM: Artificial Sequence
<220> FEATURE:
<223> OTHER INFORMATION: Description of Artificial Sequence: Fusion
      protein
```

<400> SEQUENCE: 7

```
Met Leu Pro Ile Cys Pro Gly Gly Ala Ala Arg Cys Gln Val Thr Leu
 1               5                  10                  15

Arg Asp Leu Phe Asp Arg Ala Val Val Leu Ser His Tyr Ile His Asn
             20                  25                  30

Leu Ser Ser Glu Met Phe Ser Glu Phe Asp Lys Arg Tyr Thr His Gly
         35                  40                  45

Arg Phe Ile Thr Lys Ala Ile Asn Ser Cys His Thr Ser Ser Leu Ala
 50                  55                  60

Thr Pro Glu Asp Lys Glu Gln Ala Gln Gln Met Asn Gln Lys Asp Phe
 65                  70                  75                  80

Leu Ser Leu Ile Val Ser Ile Leu Arg Ser Trp Asn Glu Pro Leu Tyr
             85                  90                  95

His Leu Val Thr Glu Val Arg Gly Met Gln Glu Ala Pro Glu Ala Ile
            100                 105                 110

Leu Ser Lys Ala Val Glu Ile Glu Glu Gln Thr Lys Arg Leu Leu Glu
        115                 120                 125

Gly Met Glu Leu Ile Val Ser Gln Val His Pro Glu Thr Lys Glu Asn
130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Leu Lys Cys Arg
            180                 185                 190

Ile Ile His Asn Asn Asn Cys Gly Ser Leu Phe Glu Lys Lys Val Tyr
        195                 200                 205

Leu Ser Glu Cys Lys Thr Gly Asn Gly Lys Asn Tyr Arg Gly Thr Met
210                 215                 220

Ser Lys Thr Lys Asn Gly Ile Thr Cys Gln Lys Trp Ser Ser Thr Ser
225                 230                 235                 240

Pro His Arg Pro Arg Phe Ser Pro Ala Thr His Pro Ser Glu Gly Leu
                245                 250                 255

Glu Glu Asn Tyr Cys Arg Asn Pro Asp Asn Asp Pro Gln Gly Pro Trp
            260                 265                 270

Cys Tyr Thr Thr Asp Pro Glu Lys Arg Tyr Asp Tyr Cys Asp Ile Leu
        275                 280                 285

Glu Cys Glu Glu Glu Cys Met His Cys Ser Gly Glu Asn Tyr Asp Gly
290                 295                 300

Lys Ile Ser Lys Thr Met Ser Gly Leu Glu Cys Gln Ala Trp Asp Ser
305                 310                 315                 320

Gln Ser Pro His Ala His Gly Tyr Ile Pro Ser Lys Phe Pro Asn Lys
                325                 330                 335

Asn Leu Lys Lys Asn Tyr Cys Arg Asn Pro Asp Arg Glu Leu Arg Pro
            340                 345                 350

Trp Cys Phe Thr Thr Asp Pro Asn Lys Arg Trp Glu Leu Cys Asp Ile
        355                 360                 365

Pro Arg Cys Thr Thr Pro Pro Ser Ser Gly Pro Thr Tyr Gln Cys
370                 375                 380

Leu Lys Gly Thr Gly Glu Asn Tyr Arg Gly Asn Val Ala Val Thr Val
385                 390                 395                 400

Ser Gly His Thr Cys Gln His Trp Ser Ala Gln Thr Pro His Thr His
                405                 410                 415
```

-continued

```
Asn Arg Thr Pro Glu Asn Phe Pro Cys Lys Asn Leu Asp Glu Asn Tyr
            420                 425                 430

Cys Arg Asn Pro Asp Gly Lys Arg Ala Pro Trp Cys His Thr Thr Asn
        435                 440                 445

Ser Gln Val Arg Trp Glu Tyr Cys Lys Ile Pro Ser Cys Asp Ser Ser
    450                 455                 460

Pro Val Ser Thr Glu Gln Leu Ala Pro Thr Ala Pro Pro Glu Leu Thr
465                 470                 475                 480

Pro Val Val Gln Asp Cys Tyr His Gly Asp Gly Gln Ser Tyr Arg Gly
                485                 490                 495

Thr Ser Ser Thr Thr Thr Thr Gly Lys Lys Cys Gln Ser Trp Ser Ser
            500                 505                 510

Met Thr Pro His Arg His Gln Lys Thr Pro Glu Asn Tyr Pro Asn Ala
        515                 520                 525

Gly Leu Thr Met Asn Tyr Cys Arg Asn Pro Asp Ala Asp Lys Gly Pro
    530                 535                 540

Trp Cys Phe Thr Thr Asp Pro Ser Val Arg Trp Glu Tyr Cys Asn Leu
545                 550                 555                 560

Lys Lys Cys Ser Gly Thr Glu Ala Ser Val Val Ala Pro Pro Pro Val
                565                 570                 575

Val Leu Leu

<210> SEQ ID NO 8
<211> LENGTH: 942
<212> TYPE: PRT
<213> ORGANISM: Artificial Sequence
<220> FEATURE:
<223> OTHER INFORMATION: Description of Artificial Sequence: Fusion
      protein

<400> SEQUENCE: 8

Met Leu Pro Ile Cys Pro Gly Gly Ala Ala Arg Cys Gln Val Thr Leu
  1               5                  10                  15

Arg Asp Leu Phe Asp Arg Ala Val Val Leu Ser His Tyr Ile His Asn
             20                  25                  30

Leu Ser Ser Glu Met Phe Ser Glu Phe Asp Lys Arg Tyr Thr His Gly
         35                  40                  45

Arg Phe Ile Thr Lys Ala Ile Asn Ser Cys His Thr Ser Ser Leu Ala
     50                  55                  60

Thr Pro Glu Asp Lys Glu Gln Ala Gln Gln Met Asn Gln Lys Asp Phe
 65                  70                  75                  80

Leu Ser Leu Ile Val Ser Ile Leu Arg Ser Trp Asn Glu Pro Leu Tyr
                 85                  90                  95

His Leu Val Thr Glu Val Arg Gly Met Gln Glu Ala Pro Glu Ala Ile
            100                 105                 110

Leu Ser Lys Ala Val Glu Ile Glu Glu Gln Thr Lys Arg Leu Leu Glu
        115                 120                 125

Gly Met Glu Leu Ile Val Ser Gln Val His Pro Glu Thr Lys Glu Asn
    130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Leu Lys Cys Arg
            180                 185                 190

Ile Ile His Asn Asn Asn Cys Gly Ser Ala Ser Val Gly Leu Pro Ser
```

-continued

```
                195                 200                 205
Val Ser Leu Asp Leu Pro Arg Leu Ser Ile Gln Lys Asp Ile Leu Thr
210                 215                 220
Ile Lys Ala Asn Thr Thr Leu Gln Ile Thr Cys Arg Gly Gln Arg Asp
225                 230                 235                 240
Leu Asp Trp Leu Trp Pro Asn Asn Gln Ser Gly Ser Glu Gln Arg Val
                245                 250                 255
Glu Val Thr Glu Cys Ser Asp Gly Leu Phe Cys Lys Thr Leu Thr Ile
                260                 265                 270
Pro Lys Val Ile Gly Asn Asp Thr Gly Ala Tyr Lys Cys Phe Tyr Arg
            275                 280                 285
Glu Thr Asp Leu Ala Ser Val Ile Tyr Val Tyr Val Gln Asp Tyr Arg
290                 295                 300
Ser Pro Phe Ile Ala Ser Val Ser Asp Gln His Gly Val Val Tyr Ile
305                 310                 315                 320
Thr Glu Asn Lys Asn Lys Thr Val Val Ile Pro Cys Leu Gly Ser Ile
                325                 330                 335
Ser Asn Leu Asn Val Ser Leu Cys Ala Arg Tyr Pro Glu Lys Arg Phe
            340                 345                 350
Val Pro Asp Gly Asn Arg Ile Ser Trp Asp Ser Lys Lys Gly Phe Thr
            355                 360                 365
Ile Pro Ser Tyr Met Ile Ser Tyr Ala Gly Met Val Phe Cys Glu Ala
            370                 375                 380
Lys Ile Asn Asp Glu Ser Tyr Gln Ser Ile Met Tyr Ile Val Val Val
385                 390                 395                 400
Val Gly Tyr Arg Ile Tyr Asp Val Val Leu Ser Pro Ser His Gly Ile
                405                 410                 415
Glu Leu Ser Val Gly Glu Lys Leu Val Leu Asn Cys Thr Ala Arg Thr
            420                 425                 430
Glu Leu Asn Val Gly Ile Asp Phe Asn Trp Glu Tyr Pro Ser Ser Lys
            435                 440                 445
His Gln His Lys Lys Leu Val Asn Arg Asp Leu Lys Thr Gln Ser Gly
450                 455                 460
Ser Glu Met Lys Lys Phe Leu Ser Thr Leu Thr Ile Asp Gly Val Thr
465                 470                 475                 480
Arg Ser Asp Gln Gly Leu Tyr Thr Cys Ala Ala Ser Ser Gly Leu Met
                485                 490                 495
Thr Lys Lys Asn Ser Thr Phe Val Arg Val His Glu Lys Pro Phe Val
            500                 505                 510
Ala Phe Gly Ser Gly Met Glu Ser Leu Val Glu Ala Thr Val Gly Glu
            515                 520                 525
Arg Val Arg Ile Pro Ala Lys Tyr Leu Gly Tyr Pro Pro Pro Glu Ile
            530                 535                 540
Lys Trp Tyr Lys Asn Gly Ile Pro Leu Glu Ser Asn His Thr Ile Lys
545                 550                 555                 560
Ala Gly His Val Leu Thr Ile Met Glu Val Ser Glu Arg Asp Thr Gly
                565                 570                 575
Asn Tyr Thr Val Ile Leu Thr Asn Pro Ile Ser Lys Glu Lys Gln Ser
            580                 585                 590
His Val Val Ser Leu Val Val Tyr Val Pro Pro Gln Ile Gly Glu Lys
            595                 600                 605
Ser Leu Ile Ser Pro Val Asp Ser Tyr Gln Tyr Gly Thr Thr Gln Thr
610                 615                 620
```

```
Leu Thr Cys Thr Val Tyr Ala Ile Pro Pro His His Ile His Trp
625                 630                 635                 640

Tyr Trp Gln Leu Glu Glu Cys Ala Asn Pro Ser Gln Ala Val
            645                 650                 655

Ser Val Thr Asn Pro Tyr Pro Cys Glu Glu Trp Arg Ser Val Glu Asp
                660                 665                 670

Phe Gln Gly Gly Asn Lys Ile Glu Val Asn Lys Asn Gln Phe Ala Leu
            675                 680                 685

Ile Glu Gly Lys Asn Lys Thr Val Ser Thr Leu Val Ile Gln Ala Ala
690                 695                 700

Asn Val Ser Ala Leu Tyr Lys Cys Glu Ala Val Asn Lys Val Gly Arg
705                 710                 715                 720

Gly Glu Arg Val Ile Ser Phe His Val Thr Arg Gly Pro Glu Ile Thr
                725                 730                 735

Leu Gln Pro Asp Met Gln Pro Thr Glu Gln Glu Ser Val Ser Leu Trp
                740                 745                 750

Cys Thr Ala Asp Arg Ser Thr Phe Glu Asn Leu Thr Trp Tyr Lys Leu
                755                 760                 765

Gly Pro Gln Pro Leu Pro Ile His Val Gly Glu Leu Pro Thr Pro Val
770                 775                 780

Cys Lys Asn Leu Asp Thr Leu Trp Lys Leu Asn Ala Thr Met Phe Ser
785                 790                 795                 800

Asn Ser Thr Asn Asp Ile Leu Ile Met Glu Leu Lys Asn Ala Ser Leu
                805                 810                 815

Gln Asp Gln Gly Asp Tyr Val Cys Leu Ala Gln Asp Arg Lys Thr Lys
                820                 825                 830

Lys Arg His Cys Val Val Arg Gln Leu Thr Val Leu Glu Arg Val Ala
                835                 840                 845

Pro Thr Ile Thr Gly Asn Leu Glu Asn Gln Thr Thr Ser Ile Gly Glu
850                 855                 860

Ser Ile Glu Val Ser Cys Thr Ala Ser Gly Asn Pro Pro Pro Gln Ile
865                 870                 875                 880

Met Trp Phe Lys Asp Asn Glu Thr Leu Val Glu Asp Ser Gly Ile Val
                885                 890                 895

Leu Lys Asp Gly Asn Arg Asn Leu Thr Ile Arg Arg Val Arg Lys Glu
                900                 905                 910

Asp Glu Gly Leu Tyr Thr Cys Gln Ala Cys Ser Val Leu Gly Cys Ala
                915                 920                 925

Lys Val Glu Ala Phe Phe Ile Ile Glu Gly Ala Gln Glu Lys
930                 935                 940

<210> SEQ ID NO 9
<211> LENGTH: 21
<212> TYPE: PRT
<213> ORGANISM: Homo sapiens

<400> SEQUENCE: 9

Ile Glu Glu Gln Thr Lys Arg Leu Leu Arg Gly Met Glu Leu Ile Val
1               5                   10                  15

Ser Gln Val His Pro
            20

<210> SEQ ID NO 10
<211> LENGTH: 21
<212> TYPE: PRT
<213> ORGANISM: Rattus sp.
```

-continued

```
<400> SEQUENCE: 10

Ile Glu Glu Gln Asn Lys Arg Leu Leu Glu Gly Ile Glu Lys Ile Ile
1               5                   10                  15

Gly Gln Ala Tyr Pro
            20

<210> SEQ ID NO 11
<211> LENGTH: 21
<212> TYPE: PRT
<213> ORGANISM: Mus musculus

<400> SEQUENCE: 11

Ile Glu Glu Gln Asn Lys Gln Leu Leu Glu Gly Val Glu Lys Ile Ile
1               5                   10                  15

Ser Gln Ala Tyr Pro
            20

<210> SEQ ID NO 12
<211> LENGTH: 21
<212> TYPE: PRT
<213> ORGANISM: Mesocricetus auratus

<400> SEQUENCE: 12

Ile Gly Glu Gln Asn Lys Arg Leu Leu Glu Gly Ile Glu Lys Ile Leu
1               5                   10                  15

Gly Gln Ala Tyr Pro
            20

<210> SEQ ID NO 13
<211> LENGTH: 21
<212> TYPE: PRT
<213> ORGANISM: Balaenoptera sp.

<400> SEQUENCE: 13

Glu Glu Glu Glu Asn Lys Arg Leu Leu Glu Gly Met Glu Lys Ile Val
1               5                   10                  15

Gly Gln Val His Pro
            20

<210> SEQ ID NO 14
<211> LENGTH: 21
<212> TYPE: PRT
<213> ORGANISM: Mustela sp.

<400> SEQUENCE: 14

Ile Glu Glu Glu Asn Arg Arg Leu Leu Glu Gly Met Glu Lys Ile Val
1               5                   10                  15

Gly Gln Val His Pro
            20

<210> SEQ ID NO 15
<211> LENGTH: 21
<212> TYPE: PRT
<213> ORGANISM: Bos sp.

<400> SEQUENCE: 15

Ile Glu Glu Gln Asn Lys Arg Leu Ile Glu Gly Met Glu Met Ile Phe
1               5                   10                  15

Gly Gln Val Ile Pro
            20

<210> SEQ ID NO 16
```

```
<211> LENGTH: 21
<212> TYPE: PRT
<213> ORGANISM: Ovis sp.

<400> SEQUENCE: 16

Glu Glu Glu Glu Asn Lys Arg Leu Leu Glu Gly Met Glu Asn Ile Phe
 1               5                  10                  15

Gly Gln Val Ile Pro
            20

<210> SEQ ID NO 17
<211> LENGTH: 21
<212> TYPE: PRT
<213> ORGANISM: Sus sp.

<400> SEQUENCE: 17

Ile Glu Glu Gln Asn Lys Arg Leu Leu Glu Gly Met Glu Lys Ile Val
 1               5                  10                  15

Gly Gln Val His Pro
            20

<210> SEQ ID NO 18
<211> LENGTH: 21
<212> TYPE: PRT
<213> ORGANISM: Camelus sp.

<400> SEQUENCE: 18

Ile Glu Glu Gln Asn Lys Arg Leu Leu Glu Gly Met Glu Lys Ile Val
 1               5                  10                  15

Gly Gln Val His Pro
            20

<210> SEQ ID NO 19
<211> LENGTH: 21
<212> TYPE: PRT
<213> ORGANISM: Equus sp.

<400> SEQUENCE: 19

Glu Ile Glu Gln Asn Arg Arg Leu Leu Glu Gly Met Glu Lys Ile Val
 1               5                  10                  15

Gly Gln Val Gln Pro
            20

<210> SEQ ID NO 20
<211> LENGTH: 21
<212> TYPE: PRT
<213> ORGANISM: Elephantidae gen. sp.

<400> SEQUENCE: 20

Val Lys Glu Glu Asn Gln Arg Leu Leu Glu Gly Ile Glu Lys Ile Val
 1               5                  10                  15

Asp Gln Val His Pro
            20

<210> SEQ ID NO 21
<211> LENGTH: 21
<212> TYPE: PRT
<213> ORGANISM: Unknown Organism
<220> FEATURE:
<223> OTHER INFORMATION: Description of Unknown Organism: Ancestral
      mammal

<400> SEQUENCE: 21

Ile Glu Glu Glu Asn Lys Arg Leu Leu Glu Gly Met Glu Lys Ile Val
```

-continued

```
               1               5                  10                 15

Gly Gln Val His Pro
            20

<210> SEQ ID NO 22
<211> LENGTH: 21
<212> TYPE: PRT
<213> ORGANISM: Gallus sp.

<400> SEQUENCE: 22

Ile Glu Glu Gln Asn Lys Arg Leu Leu Glu Gly Met Glu Lys Ile Val
  1               5                  10                 15

Gly Arg Val His Ser
            20

<210> SEQ ID NO 23
<211> LENGTH: 21
<212> TYPE: PRT
<213> ORGANISM: Meleagris gallopavo

<400> SEQUENCE: 23

Ile Glu Glu Gln Asp Lys Arg Leu Leu Glu Gly Met Glu Lys Ile Val
  1               5                  10                 15

Gly Arg Ile His Ser
            20

<210> SEQ ID NO 24
<211> LENGTH: 21
<212> TYPE: PRT
<213> ORGANISM: Unknown Organism
<220> FEATURE:
<223> OTHER INFORMATION: Description of Unknown Organism: Chelonia sp.

<400> SEQUENCE: 24

Ile Glu Glu Gln Asn Lys Arg Leu Leu Glu Gly Met Glu Lys Ile Val
  1               5                  10                 15

Gly Gln Val His Pro
            20

<210> SEQ ID NO 25
<211> LENGTH: 21
<212> TYPE: PRT
<213> ORGANISM: Crocodylus sp.

<400> SEQUENCE: 25

Ile Glu Glu Gln Asn Lys Arg Leu Leu Glu Gly Met Glu Lys Ile Ile
  1               5                  10                 15

Gly Arg Val Gln Pro
            20

<210> SEQ ID NO 26
<211> LENGTH: 21
<212> TYPE: PRT
<213> ORGANISM: Alligator sp.

<400> SEQUENCE: 26

Ile Glu Glu Gln Asn Lys Arg Leu Leu Glu Gly Met Glu Lys Val Ile
  1               5                  10                 15

Gly Arg Val Gln Pro
            20

<210> SEQ ID NO 27
<211> LENGTH: 21
```

```
<212> TYPE: PRT
<213> ORGANISM: Unknown Organism
<220> FEATURE:
<223> OTHER INFORMATION: Description of Unknown Organism: Ancestral
      amniote

<400> SEQUENCE: 27

Ile Glu Glu Gln Asn Lys Arg Leu Leu Glu Gly Met Glu Lys Ile Val
 1               5                  10                  15

Gly Gln Val His Pro
            20

<210> SEQ ID NO 28
<211> LENGTH: 21
<212> TYPE: PRT
<213> ORGANISM: Xenopus sp.

<400> SEQUENCE: 28

Val Glu Glu Gln Asn Lys Arg Leu Leu Glu Gly Met Glu Lys Ile Val
 1               5                  10                  15

Gly Arg Ile His Pro
            20

<210> SEQ ID NO 29
<211> LENGTH: 21
<212> TYPE: PRT
<213> ORGANISM: Rana sp.

<400> SEQUENCE: 29

Val Glu Glu Gln Thr Lys Arg Leu Leu Glu Gly Met Glu Arg Ile Ile
 1               5                  10                  15

Gly Arg Ile Gln Pro
            20

<210> SEQ ID NO 30
<211> LENGTH: 21
<212> TYPE: PRT
<213> ORGANISM: Neoceratodus forsteri

<400> SEQUENCE: 30

Val Glu Asp Gln Thr Lys Gln Leu Ile Glu Gly Met Glu Lys Ile Leu
 1               5                  10                  15

Ser Arg Met His Pro
            20

<210> SEQ ID NO 31
<211> LENGTH: 21
<212> TYPE: PRT
<213> ORGANISM: Tilapia sp.

<400> SEQUENCE: 31

Met Gln Gln Tyr Ser Lys Ser Leu Lys Asp Gly Leu Asp Val Leu Ser
 1               5                  10                  15

Ser Lys Met Gly Ser
            20

<210> SEQ ID NO 32
<211> LENGTH: 21
<212> TYPE: PRT
<213> ORGANISM: Tilapia sp.

<400> SEQUENCE: 32

Met Gln Glu His Ser Lys Asp Leu Lys Asp Gly Leu Asp Ile Leu Ser
 1               5                  10                  15
```

Ser Lys Met Gly Pro
            20

<210> SEQ ID NO 33
<211> LENGTH: 21
<212> TYPE: PRT
<213> ORGANISM: Cyprinus carpio

<400> SEQUENCE: 33

Leu Gln Glu Asn Ile Asn Ser Leu Gly Ala Gly Leu Glu His Val Phe
1               5                   10                  15

Asn Lys Met Asp Ser
            20

<210> SEQ ID NO 34
<211> LENGTH: 21
<212> TYPE: PRT
<213> ORGANISM: Hypophthalmichthys nobilis

<400> SEQUENCE: 34

Leu Gln Asp Asn Ile Asn Ser Leu Gly Ala Gly Leu Glu Arg Val Val
1               5                   10                  15

His Lys Met Gly Ser
            20

<210> SEQ ID NO 35
<211> LENGTH: 21
<212> TYPE: PRT
<213> ORGANISM: Hypophthalmichthys molitrix

<400> SEQUENCE: 35

Leu Gln Asp Asn Ile Asn Ser Leu Val Pro Gly Leu Glu His Val Val
1               5                   10                  15

His Lys Met Gly Ser
            20

<210> SEQ ID NO 36
<211> LENGTH: 21
<212> TYPE: PRT
<213> ORGANISM: Oncorhynchus keta

<400> SEQUENCE: 36

Leu Gln Asp Tyr Ser Lys Ser Leu Gly Asp Gly Leu Asp Ile Met Val
1               5                   10                  15

Asn Lys Met Gly Pro
            20

<210> SEQ ID NO 37
<211> LENGTH: 21
<212> TYPE: PRT
<213> ORGANISM: Oncorhynchus tshawytscha

<400> SEQUENCE: 37

Leu Gln Asp Tyr Ser Lys Ser Leu Gly Asp Gly Leu Asp Ile Met Val
1               5                   10                  15

Asn Lys Met Gly Pro
            20

<210> SEQ ID NO 38
<211> LENGTH: 21
<212> TYPE: PRT
<213> ORGANISM: Salmo sp.

-continued

<400> SEQUENCE: 38

Leu Gln Asp Tyr Ser Lys Ser Leu Gly Asp Gly Leu Asp Ile Met Val
1               5                   10                  15

Asn Lys Met Gly Pro
            20

<210> SEQ ID NO 39
<211> LENGTH: 22
<212> TYPE: PRT
<213> ORGANISM: Homo sapiens

<400> SEQUENCE: 39

Val Tyr Asp Leu Leu Lys Asp Leu Glu Glu Gly Ile Gln Thr Leu Met
1               5                   10                  15

Arg Glu Leu Glu Asp Gly
            20

<210> SEQ ID NO 40
<211> LENGTH: 22
<212> TYPE: PRT
<213> ORGANISM: Bos sp.

<400> SEQUENCE: 40

Val Tyr Glu Lys Leu Lys Asp Leu Glu Glu Gly Ile Leu Ala Leu Met
1               5                   10                  15

Arg Glu Leu Glu Asp Gly
            20

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
catatgttgc ccatctgtcc cggc                                          24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggatccgcag ttgttgttgt ggat                                          24

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggatcccaca gccaccgcga cttccag                                       27

<210> SEQ ID NO 44
<211> LENGTH: 29
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 44
ctcgagctac ttggaggcag tcatgaagc                                             29

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
catatgcaca gccaccgcga cttccag                                               27
```